(12) United States Patent
Brown et al.

(10) Patent No.: US 11,464,531 B2
(45) Date of Patent: *Oct. 11, 2022

(54) TISSUE INCISION DEVICE

(71) Applicant: Release Medical, Inc., Campbell, CA (US)

(72) Inventors: Treg Brown, Carbondale, IL (US); Steven S. Golden, Menlo Park, CA (US); Robert Fernandez, Campbell, CA (US); Nathaniel Cohen, Los Gatos, CA (US)

(73) Assignee: RELEASE MEDICAL, INC., Campbell, CA (US)

( * ) Notice: Subject to any disclaimer, the term of this patent is extended or adjusted under 35 U.S.C. 154(b) by 449 days.

This patent is subject to a terminal disclaimer.

(21) Appl. No.: 16/505,216

(22) Filed: Jul. 8, 2019

(65) Prior Publication Data

US 2019/0343546 A1 Nov. 14, 2019

Related U.S. Application Data

(63) Continuation of application No. 15/629,605, filed on Jun. 21, 2017, now Pat. No. 10,413,313, which is a
(Continued)

(51) Int. Cl.
*A61B 18/18* (2006.01)
*A61B 17/32* (2006.01)
(Continued)

(52) U.S. Cl.
CPC .. *A61B 17/320016* (2013.01); *A61B 10/0275* (2013.01); *A61B 17/32002* (2013.01);
(Continued)

(58) Field of Classification Search
CPC ........ A61B 10/0275; A61B 17/320016; A61B 17/32002; A61B 17/3421; A61B 17/3472;
(Continued)

(56) References Cited

U.S. PATENT DOCUMENTS 3,007,471 A 11/1961 McClure, Jr. et al.
3,347,232 A 10/1967 Ginsburg
(Continued)

FOREIGN PATENT DOCUMENTS

CA 2890477 6/2014
CN 1411355 4/2003
(Continued)

OTHER PUBLICATIONS

U.S. Appl. No. 15/025,168, "Advisory Action", dated Apr. 27, 2018, 5 pages.
(Continued)

*Primary Examiner* — Michael F Peffley
*Assistant Examiner* — Amanda L Zink
(74) *Attorney, Agent, or Firm* — Kilpatrick Townsend & Stockton LLP

(57) ABSTRACT

A minimally invasive tissue incision system for creating joint capsulotomies and releasing/incising various tissues, tendons, and fibrous band structures is described. The system contains a penetrating needle which is retractable so as to expose a cutting element, and which may be used as a penetrating needle to pierce the skin and other soft tissue structures. The cutting element provided within the penetrating needle may be used to incise subsequent tissue structures after the initial penetration. The system facilitates such procedures by providing the cutting element with the confines of the needle which provides safe introduction of the cutting element directly to the site via the needle.

20 Claims, 13 Drawing Sheets

Related U.S. Application Data continuation of application No. 15/025,168, filed as application No. PCT/US2014/057857 on Sep. 26, 2014, now abandoned.

(60) Provisional application No. 61/912,439, filed on Dec. 5, 2013, provisional application No. 61/883,861, filed on Sep. 27, 2013.

(51) Int. Cl.
| | |
|---|---|
| *A61B 10/02* | (2006.01) |
| *A61B 17/34* | (2006.01) |
| *A61B 18/14* | (2006.01) |
| *A61B 18/12* | (2006.01) |

(52) U.S. Cl.
CPC ...... *A61B 17/3421* (2013.01); *A61B 17/3472* (2013.01); *A61B 17/3496* (2013.01); *A61B 18/148* (2013.01); *A61B 18/1233* (2013.01); *A61B 2017/320004* (2013.01); *A61B 2017/320008* (2013.01)

(58) Field of Classification Search
CPC ............ A61B 17/3496; A61B 18/1233; A61B 18/1477; A61B 18/148; A61B 2017/320004; A61B 2017/320008; A61B 2018/00601; A61B 2218/002
See application file for complete search history.

(56) References Cited

U.S. PATENT DOCUMENTS

| | | | |
|---|---|---|---|
| 4,444,184 A | 4/1984 | Oretorp | |
| 4,491,132 A | 1/1985 | Aikins et al. | |
| 4,642,090 A | 2/1987 | Utrata | |
| 4,790,312 A | 12/1988 | Piraino et al. | |
| 5,029,573 A | 7/1991 | Chow | |
| 5,234,436 A | 8/1993 | Santamaria et al. | |
| 5,254,128 A | 10/1993 | Mesa et al. | |
| 5,273,024 A | 12/1993 | Menon et al. | |
| 5,275,606 A | 1/1994 | Abidin et al. | |
| 5,306,284 A | 4/1994 | Agee et al. | |
| 5,312,413 A | 5/1994 | Santamaria et al. | |
| 5,320,110 A * | 6/1994 | Wang ................ | A61B 10/0275 600/566 |
| 5,323,765 A | 6/1994 | Brown | |
| 5,330,432 A * | 7/1994 | Yoon ................ | A61B 17/3417 604/164.12 |
| 5,334,214 A | 8/1994 | Putman et al. | |
| 5,356,419 A | 10/1994 | Chow | |
| 5,366,465 A | 11/1994 | Mirza | |
| 5,441,502 A | 8/1995 | Bartlett | |
| 5,462,062 A | 10/1995 | Rubinstein et al. | |
| 5,569,283 A | 10/1996 | Nolan et al. | |
| 5,571,215 A * | 11/1996 | Sterman ........... | A61B 17/00234 128/898 |
| 5,620,454 A | 4/1997 | Pierce et al. | |
| 5,730,749 A | 3/1998 | Battenfield | |
| 5,769,086 A * | 6/1998 | Ritchart ............ | A61B 10/0275 600/566 |
| 5,769,865 A | 6/1998 | Kermode et al. | |
| 6,019,774 A | 2/2000 | Weiss et al. | |
| 6,068,603 A | 5/2000 | Suzuki et al. | |
| 6,179,852 B1 | 1/2001 | Strickland et al. | |
| 6,224,574 B1 | 5/2001 | Al-Labban et al. | |
| 6,270,501 B1 | 8/2001 | Freiberg et al. | |
| 6,685,717 B1 | 2/2004 | Ilic | |
| 6,974,476 B2 | 12/2005 | McGuckin, Jr. et al. | |
| 7,491,177 B2 | 1/2009 | Hibner | |
| 7,553,307 B2 | 6/2009 | Bleich et al. | |
| 7,641,658 B2 | 1/2010 | Shaolian et al. | |
| 7,780,690 B2 | 8/2010 | Rehnke et al. | |
| 7,799,032 B2 | 9/2010 | Assell et al. | |
| 7,918,784 B2 | 4/2011 | Peimer et al. | |
| 8,088,136 B2 | 1/2012 | Berberich | |
| 8,256,330 B2 | 9/2012 | Galewyrick et al. | |
| 8,256,331 B2 | 9/2012 | Galewyrick et al. | |
| 8,257,379 B2 | 9/2012 | Lee et al. | |
| 8,273,098 B2 | 9/2012 | Strickland et al. | |
| 8,328,836 B2 | 12/2012 | Conlon et al. | |
| 8,348,966 B2 | 1/2013 | Liou et al. | |
| 8,377,086 B2 | 2/2013 | Flynn et al. | |
| 8,403,863 B2 | 3/2013 | Al Mohizea et al. | |
| 8,460,289 B2 | 6/2013 | Sartor | |
| 8,485,988 B2 | 7/2013 | Flatland et al. | |
| 8,523,903 B2 | 9/2013 | Kilburn-Peterson et al. | |
| 8,753,364 B2 | 6/2014 | Liou et al. | |
| 10,413,313 B2 | 9/2019 | Brown et al. | |
| 2002/0143352 A1 | 10/2002 | Newman et al. | |
| 2003/0097079 A1 | 5/2003 | Garcia et al. | |
| 2004/0181246 A1 | 9/2004 | Heppler et al. | |
| 2006/0190021 A1 | 8/2006 | Hausman et al. | |
| 2007/0250057 A1 | 10/2007 | Nobis et al. | |
| 2008/0091196 A1 | 4/2008 | Deal et al. | |
| 2009/0048620 A1 | 2/2009 | Weiss et al. | |
| 2009/0112119 A1 * | 4/2009 | Kim ................... | A61B 10/0275 600/564 |
| 2009/0157110 A1 | 6/2009 | Muto et al. | |
| 2009/0234274 A1 | 9/2009 | Luloh et al. | |
| 2009/0275970 A1 * | 11/2009 | Leibowitz .......... | A61B 17/3496 606/185 |
| 2009/0312782 A1 | 12/2009 | Park et al. | |
| 2010/0268175 A1 | 10/2010 | Lunsford et al. | |
| 2011/0046652 A1 | 2/2011 | Rehnke et al. | |
| 2011/0087250 A1 | 4/2011 | Ricol et al. | |
| 2011/0087258 A1 | 4/2011 | Sluss et al. | |
| 2011/0087260 A1 | 4/2011 | Seipel et al. | |
| 2011/0172682 A1 | 7/2011 | Brady et al. | |
| 2012/0029542 A1 | 2/2012 | Huang et al. | |
| 2012/0065695 A1 | 3/2012 | Ishii et al. | |
| 2012/0108926 A1 * | 5/2012 | Kassab ............. | A61B 17/3403 600/323 |
| 2012/0157999 A1 | 6/2012 | Ochiai et al. | |
| 2012/0221032 A1 | 8/2012 | Duperier et al. | |
| 2012/0226299 A1 | 9/2012 | Heppler et al. | |
| 2012/0232571 A1 | 9/2012 | Muto et al. | |
| 2012/0239070 A1 | 9/2012 | Wijay et al. | |
| 2013/0006232 A1 | 1/2013 | Pellegrino et al. | |
| 2013/0006323 A1 | 1/2013 | Tal et al. | |
| 2013/0110146 A1 | 5/2013 | McCormack et al. | |
| 2014/0031865 A1 | 1/2014 | Kilburn-Peterson et al. | |
| 2015/0320481 A1 * | 11/2015 | Cosman, Jr. ........ | A61B 18/16 606/35 |
| 2016/0235431 A1 | 8/2016 | Brown et al. | |
| 2017/0281214 A1 | 10/2017 | Brown et al. | |

FOREIGN PATENT DOCUMENTS

| | | |
|---|---|---|
| CN | 1440728 | 9/2003 |
| CN | 2712278 | 7/2005 |
| CN | 201135459 | 10/2008 |
| CN | 201211201 | 3/2009 |
| CN | 105899153 | 8/2016 |
| EP | 3038549 | 7/2016 |
| JP | 2012525160 | 10/2012 |
| JP | 2012236071 | 12/2012 |
| JP | 2013516292 | 5/2013 |
| JP | 2013534156 | 9/2013 |
| JP | 6321272 | 4/2018 |
| KR | 1020020065485 | 8/2002 |
| WO | 9604851 | 2/1996 |
| WO | 9635380 | 11/1996 |
| WO | 2007120727 | 10/2007 |
| WO | 2013138482 | 9/2013 |
| WO | 2015048545 | 4/2015 |

OTHER PUBLICATIONS

U.S. Appl. No. 15/025,168, "Final Office Action", dated Feb. 22, 2018, 11 pages.
U.S. Appl. No. 15/025,168, "Non-Final Office Action", dated Aug. 25, 2017, 10 pages.

(56) References Cited

OTHER PUBLICATIONS

U.S. Appl. No. 15/025,168, "Non-Final Office Action", dated Aug. 28, 2018, 10 pages.
U.S. Appl. No. 15/629,605, "Advisory Action", dated Apr. 27, 2018, 5 pages.
U.S. Appl. No. 15/629,605, "Corrected Notice of Allowability", dated May 1, 2019, 2 pages.
U.S. Appl. No. 15/629,605, "Final Office Action", dated Feb. 22, 2018, 13 pages.
U.S. Appl. No. 15/629,605, "Non-Final Office Action", dated Aug. 31, 2018, 11 pages.
U.S. Appl. No. 15/629,605, "Non-Final Office Action", dated Sep. 6, 2017, 11 pages.
U.S. Appl. No. 15/629,605, "Notice of Allowance", dated Apr. 4, 2019, 8 pages.
CA29253313, "Office Action", dated Apr. 19, 2016, 3 pages.
CA2925313, "Notice of Allowance", dated Jul. 21, 2016, 1 page.
CN201480059401.2, "Office Action", dated Jun. 26, 2018, 15 pages.
CN201480059401.2, "Office Action", dated Jan. 17, 2019, 19 pages.
CN201480059401.2, "Office Action", dated Oct. 26, 2017, 8 pages.
EP14848549.3, "Extended European Search Report", dated Sep. 1, 2016, 7 pages.
EP14848549.3, "Notice of Decision to Grant", dated Jul. 11, 2019, 2 pages.
EP14848549.3, "Office Action", dated Apr. 23, 2018, 5 pages.
EP14848549.3, "Office Action", dated Jul. 28, 2017, 5 pages.
JP2016-518103, "OfficeAction", dated Sep. 5, 2016, 11 pages.
JP2016-518103, "Office Action", dated Feb. 24, 2017, 3 pages.
JP2017-123615, "Notice of Allowance", dated Mar. 6, 2018, 3 pages.
JP2017-123615, "Office Action", dated Sep. 21, 2017, 14 pages.
KR10-2016-7010939, "Office Action", dated Jan. 31, 2017, 7 pages.
KR10-2016-7010939, "Office Action", dated Jul. 24, 2017, 8 pages.
KR10-2016-7010939, "Office Action", dated Sep. 1, 2017, 8 pages.
KR10-2016-7010939, "Office Action", dated Jul. 27, 2016, 9 pages.
PCT/US2014/057857, "International Search Report and Written Opinion", dated Feb. 24, 2015, 10 pages.
PCT/US2014/057857, "Invitation to Pay Additional Fees and Partial Search Report", dated Dec. 22, 2014, 2 pages.

\* cited by examiner

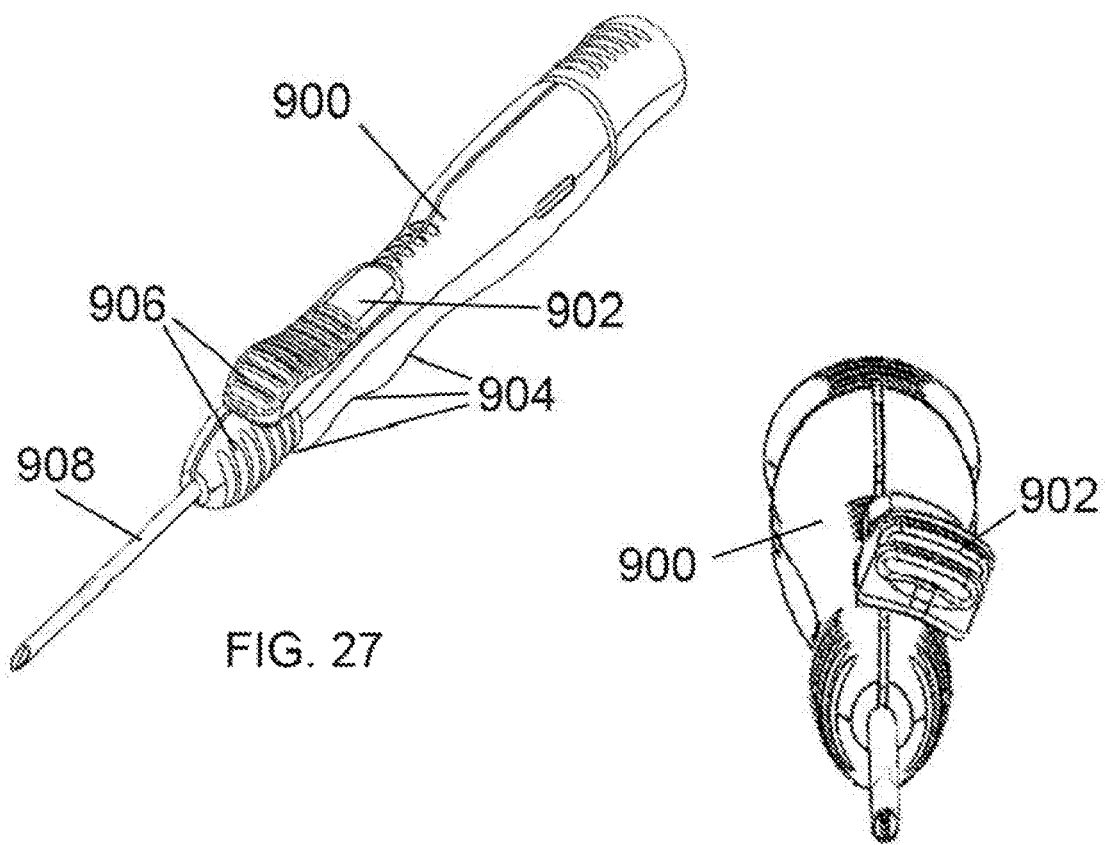
FIG. 27
FIG. 28
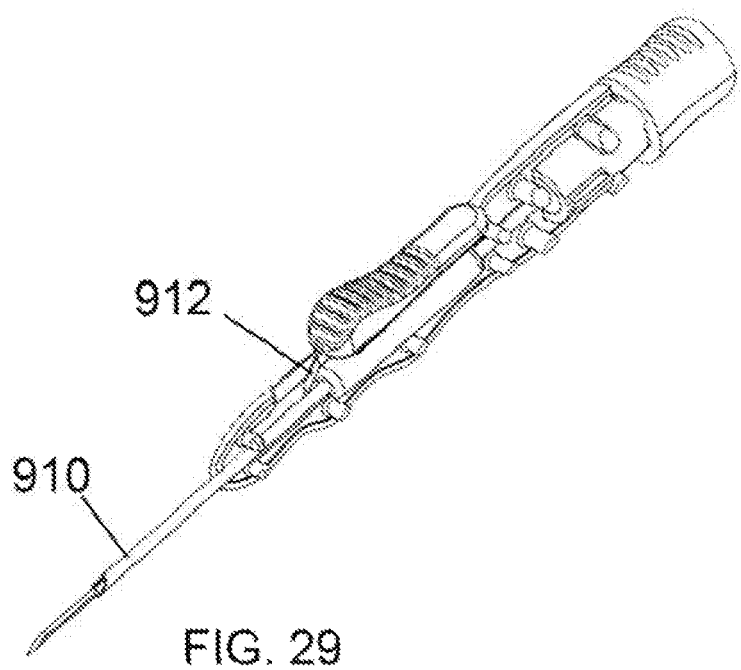
FIG. 29

TISSUE INCISION DEVICE

CROSS-REFERENCES TO RELATED APPLICATIONS

This application is a continuation of U.S. patent application Ser. No. 15/629,605, filed Jun. 21, 2017, which was granted on Sep. 17, 2019 as U.S. Pat. No. 10,413,313, which application is a continuation of U.S. patent application Ser. No. 15/025,168, filed Mar. 25, 2016, which application is a U.S. 371 of International Application No, PCT/US14/57857, filed Sep. 26, 2014, which application claims the benefit of U.S. Provisional Application No. 61/883,861, filed Sep. 27, 2013 and U.S. Provisional Application No. 61/912,439, filed Dec. 5, 2013, the entire contents of which are hereby incorporated by reference in their entirety for all purposes.

BACKGROUND

There is an ever-increasing demand for more minimally invasive surgical techniques. The lower morbidity seen in percutaneous, endoscopic and arthroscopic surgery makes these techniques very appealing to both patients and physicians. These technologically advanced procedures include many forms of tissue incision at all points during the procedure. Procedures such as arthroscopic rotator cuff and labral repair, hip arthroscopy, and knee and elbow arthroscopy utilize incisions at the both the skin level and deeper-lying tissue structures. Other procedures, known generally known as "release" procedures utilize a skin incision as well as a subsequent incision in a fibrous band of tissue in order to "release" the fibrous band of tissue or allow it more freedom to move. These procedures are commonly performed by a physician in an open setting, but increasingly performed in an arthroscopic (i.e., with use of a tiny camera) setting and even performed percutaneously with only a needle penetration at the skin level. These percutaneous procedures typically require some type of visual guidance, such as endoscopy or ultrasound in order to reduce risk and assure good results. Such procedures may include plantar fascia release, carpal tunnel release, or illeotibial band release.

Because most of these procedures involve the extremities (hands, feet, arms, etc.), it is desirable to make the smallest possible incision at the skin level to minimize soft tissue damage and scarring as well as speed the healing process. This presents a great challenge regarding the size of the instrumentation used and size of the visualization systems. Typically these procedures require multiple instruments which are often switched-out with other instruments to perform the wide variety of functions. As in the case of arthroscopic joint procedures, the fibrous capsule surrounding the joint must be penetrated and opened (called a capsulotomy). This is currently done via a series of steps starting with a small gage needle (e.g., a spinal needle). Fluoroscopy is used to visualize the needle placement into the joint space. The needle must then be withdrawn and a scalpel blade inserted, sometimes blind, to further open the capsule. It can be problematic to achieve the same path through the tissue with the secondary blade, resulting in unnecessary tissue damage and procedure time. A guide pin is often used and devices such as Sluss US2011/0087258 are designed with a secondary lumen to slide over the guide pin and subsequently cut tissue but this presents the logistical issue of multiple exchanges, which adds time and complexity to the procedure. Other devices such as McCormack U.S. Pat. No. 8,753,364 are specifically designed to cut ligaments (e.g. carpal ligament) in a minimally invasive fashion using a serrated saw-type instrument, but do not allow for direct penetration of the skin and underlying tissue via an integral needle.

Currently a solution does not exist which provides cutting capability within a small bore hypodermic needle.

The following references may be relevant to this technology:

| | |
|---|---|
| Agee | 5,306,284 |
| Abidin | 5,275,606 |
| Aikins | 4,491,132 |
| Assell | 7,799,032 |
| Auchter | 8,256,331 |
| Auchter | 8,256,330 |
| Al-Laban | 6,224,574 |
| Bartlett | 5,441,502 |
| Battenfield | 5,730,749 |
| Berberich | 8,088,136 |
| Bleich | 7,553,307 |
| Brown | 5,323,765 |
| Capuano | 4,790,312 |
| Chow | 5,029,573 |
| Chow | 5,356,419 |
| Conlon | 8,328,836 |
| Deal | 2008/0091196 |
| Duperier | 2012/0221032 |
| Eaton | 5,234,436 |
| Eaton | 5,312,413 |
| Flatland | 8,485,988 |
| Flynn | 8,377,086 |
| Freiberg | 6,270,501 |
| Garcia | 2003/0097079 |
| Ginsberg | 3,347,232 |
| Green | 5,569,283 |
| Heppler | 2004/0181246 |
| Heppler | 2012/0226299 |
| Huang | 2012/0029542 |
| Kermode | 5,769,865 |
| Kilburn-Peterson | 2014/0031865 |
| Kilburn-Peterson | 8,523,903 |
| Lee | 8,257,379 |
| Liu | CN201211201 |
| McClure | 3,007,471 |
| McGukin | 6,974,476 |
| McCormack | 8,348,966 |
| McCormack | 2013/0110146 |
| Menon | 5,273,024 |
| Mesa | 5,254,128 |
| Mirza | 5,366,465 |
| Mohizea | 8,403,863 |
| Muto | 2012/0232571 |
| Muto | 2009/0157110 |
| Newman | 2002/0143352 |
| Nobis | 2007/0250057 |
| Ochiai | 2012/0157999 |
| Oretorp | 4,444,184 |
| Park | 2009/0312782 |
| Pierce | 5,620,454 |
| Pilo | WO 96/35380 |
| Putnam | 5,334,214 |
| Rehnke | 7,780,690 |
| Rehnke | 2011/0046652 |
| Rubinstein | 5,462,062 |
| Sartor | 8,460,289 |
| Seipel | 2011/0087260 |
| Sergio | 6,685,717 |
| Shaolian | 7,641,658 |
| Sluss | 2011/0087258 |
| Strickland | 6,179,852 |
| Strickland | 8,273,098 |
| Suzuki | 6,068,603 |
| Utrata | 4,642,090 |
| Weiss | 6,019,774 |
| Weiss | 2009/0048620 |
| Wellborn | 7,918,784 |
| Wijay | 2012/0239070 |

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Embodiments proposed herein solve the above issues by providing a minimally invasive tissue incision system (referred to at points herein as a "needle-knife") having a tissue cutting mechanism within a penetrating needle. The penetrating needle is used to initiate a procedure. With such a device, a capsulotomy may be created without the need for withdrawing the needle, thus reducing the risk associated with bladed instrument exchanges.

In release-type procedures, a fibrous tissue band generally requires incising in order to restore some functionality. While sometimes performed arthroscopically (with a camera), these procedures are also performed with the use of ultrasound guidance. Ultrasound guidance provides the advantage of not requiring a camera (and associated cannula) to be inserted into the working space since the ultrasound probe resides outside the patient. In these procedures, ultrasound is used to visualize the needle penetration to the desired location. A cutting or debriding tool may then directly placed or inserted via the needle lumen to incise the fibrous tissue band. In accordance with embodiments described herein, the proposed needle-knife facilitates such procedures by providing the cutting element within the confines of the needle, which provides safe introduction of the cutting element directly to the site via the needle.

An issue encountered during laparoscopic surgery is the need for an additional cutting instrument in the field without adding an additional laparoscopic port. Adding a laparoscopic port can be costly and take more time. More importantly however, adding an additional port is more invasive, typically requiring a skin incision of between 5 mm and 12 mm. In accordance with embodiments described herein, when the needle-knife is used instead of adding another laparoscopic port, it may be possible to avoid an additional incision since only the needle (2 mm diameter) penetration is required. The necessity of stitching another incision closed at the end of the procedure is also avoided.

The minimally invasive tissue incision system in accordance with embodiments herein may be used as a penetrating needle to pierce the skin and other soft tissue structures. A cutting mechanism is provided within the penetrating needle which may be used to incise subsequent tissue structures after the initial penetration.

In embodiments, the cutting element may be disposed at the end of a stylet coaxially disposed within the lumen of the needle. The cutting element/stylet is slideable within the needle and may be completely removable from the primary needle assembly so as to allow other instruments or fluids to be passed down the lumen of the needle. A luer fitting is preferably situated at the proximal end of the device to facilitate connection of the stylet and/or ancillary devices. The penetrating needle, being coaxially slideable about the stylet/cutting element, may be configured with a slider so as to facilitate retraction of the needle relative to the stylet/cutting element. Said retraction of the needle exposes the cutting element at the distal tip of the needle thus allowing tissue to be incised via movement of the entire assembly.

The needle may be further configured with a spring mechanism so as to facilitate the needle's retraction relative to the stylet/cutting element.

In embodiments, the stylet may be configured such that the distal most portion occludes the distal lumen of the needle so as to prevent tissue or other debris from becoming lodged within the needle lumen. In this configuration, the cutting element is situated just proximal of the occluding portion, which is preferably a relatively thin section, like a plate.

In further embodiments, the penetrating needle may have a window situated just proximal to the distal needle tip. Coaxially and rotatably situated within the penetrating needle is a second, inner tubular structure with a window opposite that of the window on the needle. The stylet/cutting element resides within the inner tubular structure. When the window on the inner tube is rotated to align with the window on the outer needle, the cutting element is exposed, thus allowing tissue to be incised via movement of the entire assembly. The inner tubular structure may be configured with a rotator knob at the proximal end so as to facilitate rotation of the tube to align the windows and expose the cutting element.

In embodiments, the proximal end of the device may be configured as a slender hub, similar to that of a typical spinal needle. This configuration facilitates fingertip control. In other embodiments, the proximal end of the device may be configured into a larger handle, meant to be grasped or gripped in the palm of the hand.

In other embodiments, methods for performing various "release" procedures are disclosed. These methods involve the acts of: 1) percutaneous insertion of the needle-knife into the region containing fibrous band to be released; 2) retracting the needle component to expose the cutting blade; 3) using the exposed blade to incise the fibrous band thus providing "release;" and 4) extending the needle (reverse of act 2) to cover or sheath the cutting blade and removing the assemble from the tissue.

In additional embodiments, a method of performing a joint capsulotomy is disclosed. The method involves the acts of: 1) inserting the needle-knife into the joint space; 2) retracting the needle component of the needle-knife a specified distance so as to expose a cutting element; and 3) completing the capsulotomy with the cutting element of the needle-knife. Further acts of the method may include: 4) removing the stylet/cutting element from the needle-knife and inserting a guide wire/pin through the lumen of the needle to facilitate insertion of other instrumentation.

In additional embodiments, a method of incising tissue in medical procedure comprises inserting a needle through the skin and subcutaneous tissue layers of a human or animal. The needle tip is positioned near a secondary tissue structure to be incised and the needle is retracted to expose a cutting element. The cutting element is manipulated to incise the tissue structure.

In embodiments, the incised tissue structure is a joint capsule or is a ligament or fibrous band of tissue. The initial needle penetration does not require a skin incision with another instrument. The retraction of the needle utilizes a spring. The cutting element is slidably received within the needle, and retracting the needle comprises movement of the needle proximally relative to the cutting element.

In additional embodiments, a device for incising tissue in the human body comprises a tissue-penetrating needle. The needle comprises a distal end, and a lumen extending along a length of the needle. A cutting element slidingly received within the lumen needle, and a mechanism for moving the needle relative to the cutting element. The cutting element is arranged such that it extends orthogonally to the axis of the needle and the cutting element has multiple cutting edges. The cutting element may also have serrations. The needle moves linearly along the length of an axis of the cutting element. The needle moves rotationally relative to the cutting element. The cutting element is mounted to a stylet and the stylet is designed to occlude the lumen of the needle.

In additional embodiments, the device further comprises an injector for injecting fluids through the lumen of the needle. The device further comprises an electrosurgical generator connected to the device. The device further comprises a nerve stimulation generator and monitoring device connected to the needle.

In embodiments, a device for incising tissue in the human body, comprises a body having a cutting element extending therefrom and a needle retractably secured to the body and surrounding the cutting element. The needle comprises a distal end with a tissue-penetrating point and a lumen extending along a length of the needle to an opening at the distal end. The needle is moveable relative to the body between a first position wherein the cutting element is entirely within the lumen of the needle and a second position wherein the cutting element is exposed through the opening.

In additional embodiments, the cutting element is arranged such that it extends orthogonally to the axis of the needle and the cutting element has multiple cutting edges. The cutting element may also have serrations. The needle moves linearly along the length of an axis of the cutting element. The needle may move rotationally relative to the cutting element. The cutting element is mounted to a stylet and the stylet is designed to occlude the lumen of the needle. The device further comprises an injector for injecting fluids through the lumen of the needle. The device further comprises an electrosurgical generator connected to the device. The device further comprises a nerve stimulation generator and monitoring device connected to the needle.

For a more comprehensive understanding of the nature and advantages of the present invention, reference should be made to the ensuing detailed description and accompanying drawings.

BRIEF DESCRIPTION OF THE DRAWINGS

FIG. 27 is a perspective view of an embodiment of a needle knife device enhanced for manufacturability and ergonomics and having a needle-locking feature.

FIG. 28 is a front, perspective view of the needle knife device of FIG. 27.

FIG. 29 is a partial cut-away perspective view of a needle knife device with a needle-locking feature and a biasing member.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Embodiments proposed herein provide a minimally invasive tissue incision system (referred to at points herein as a "needle-knife") having a tissue cutting mechanism or other structure within a penetrating needle. The penetrating needle is used to initiate a procedure, and the cutting mechanism or other structure is available in the penetrated opening of the entered tissue. The needle-knife disclosed herein has a broad application in orthopedic surgery as well as general laparoscopic surgery. Procedures supported by devices disclosed herein include: creation of joint capsulotomies in arthroscopic procedures of the hip and shoulder; tenotomy in the shoulder, including the rotator cuff tendon for partial thickness rotator cuff repairs; tenotomy in the biceps tendon for biceps tenodesis procedures; incision of the transverse humeral ligament; tenotomies of the hip include the psoas tendon; and tenotomy of the extensor carpiradialis brevis tendon to treat lateral epicondylitis of the elbow as well as tentotomy of the medial flexor wad for medial epicondylitis. Procedures related to the knee suitable for the device may be patella or quadriceps tenodesis, and illeotibial band release and incision of the lateral patellar retinaculum. The needle-knife device may be suitable for performing percutaneous plantar fascia release in the foot and lengthening of the Achilles tendon in the ankle area. In the leg, anterior and lateral compartment fasciotomies may be performed with the device. The device would have application for carpal tunnel syndrome to percutaneously release the carpal ligament. A1 pulley release for treatment of trigger finger condition is another application. This is intended to be a partial list demonstrating some non-limiting examples of the wide range of applications in orthopedic surgery for the technologies disclosed herein.

Applications outside of orthopedic surgery include use as an additional blade for laparoscopic surgery without the need for adding an additional port. Procedures such as laparoscopic cholecystectomy and hernia repair may encounter a need for another cutting blade in the field. Because this device is a needle, it may introduce a cutting blade to the field percutaneously. This would save time and money in the procedure.

Figure 1:
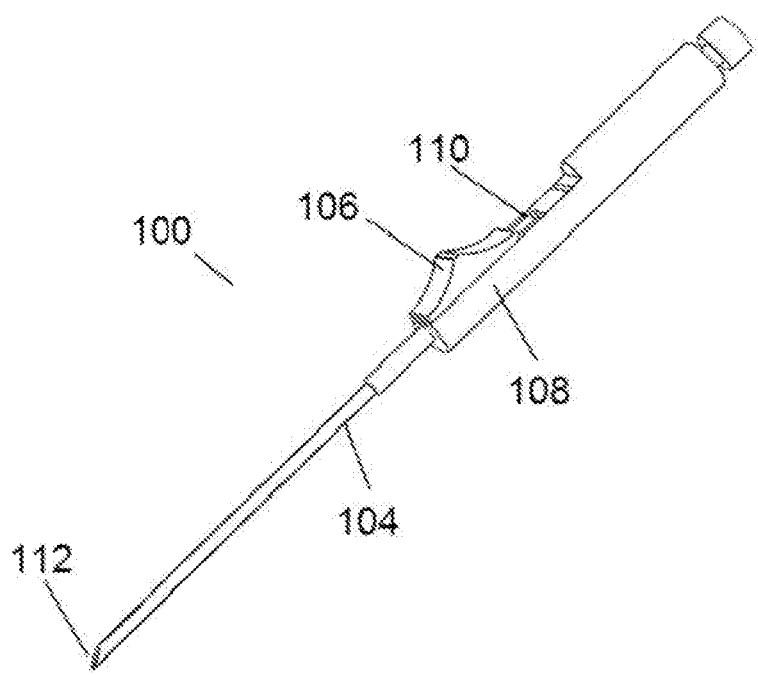
FIG. 1 is a perspective view of a needle-knife device with a needle extended in a neutral state.

Referring now to the drawings, in which like reference numerals represent like parts throughout the several views, FIG. 1 is a perspective view a needle-knife device 100 with a cutting member 102 (FIG. 3) sheathed within a penetrating needle 104. This position represents an initial state in which the device 100 would be manipulated to penetrate the needle 104 through animal or human skin and into underlying tissue. The penetrating needle 104 is shown fixedly attached at the proximal end to a slider 106 which is linearly slideable within a housing 108. In embodiments the slider 106 may be rotationally slideable as well, so as to lock into a secondary slot(s) (not shown in FIG. 1) which may extend from a primary slot 110 within the housing 108. Movement of the slider 106 directly translates to movement of the needle 104. This figure shows a simple friction slider, however other embodiments may employ a spring mechanism to facilitate movement of the slider and associated needle. Alternate embodiments may use a mechanism other than a slider to facilitate movement of the needle. An example of such a mechanism would be a thumb wheel mounted within the housing 108 and having gear teeth so as to mesh with teeth or grooves on the proximal end of the needle 104 such that rotation of said thumb wheel drives the needle backward and forward. Another example of such a mechanism is a trigger mechanism which may be used in combination with a housing that takes a pistol grip form.

In operation, the user grips the needle-knife device 100 at the housing 108 and penetrates the skin and underlying tissue with the distal tip 112 of the needle 104. Once the needle 104 is in the desired position as evidenced by visualization (ultrasound, endoscopic, or otherwise) or palpation, the user activates the slider 106 by moving the slider to a more proximal position, thus retracting the needle 104 relative a cutting element 102 (best shown in FIG. 3) so as to expose the cutting element. With the cutting element 102 exposed, the user manipulates the device as necessary so that the cutting element can cut tissue structures as desired.

Figure 2:
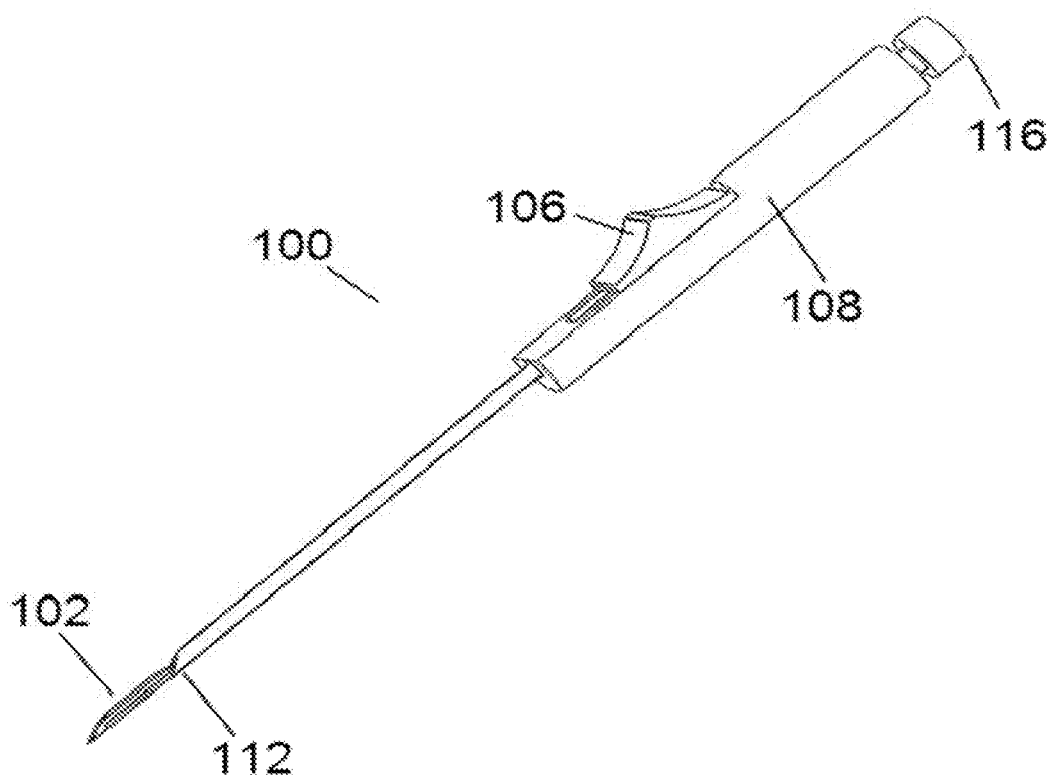
FIG. 2 is a perspective view of the needle-knife device of FIG. 1 with the needle retracted, exposing a cutting element.

FIG. 2 shows the needle-knife device 100 with the needle 104 in a retracted state. In this state the cutting element 102 is exposed from the distal tip 112 of the needle. The slider 106 is in the fully retracted position. In embodiments, a detent mechanism may be employed between the slider and the housing 108 so as to allow selective partial retraction of the needle 104. In the embodiment shown, friction can be provided between the components to allow for infinite selective retraction. The cutting member 102 is disposed at the end of a stylet 114 (shown in FIG. 3). The stylet 114 can be composed of a rod, tube, or other shaped elongated member which is attached to a hub 116 at the proximal end. The stylet 114 is mounted in the housing 108 (shown in FIG. 3). With the cutting member exposed, tissue or structures may be incised by manipulating the device.

Figure 3:
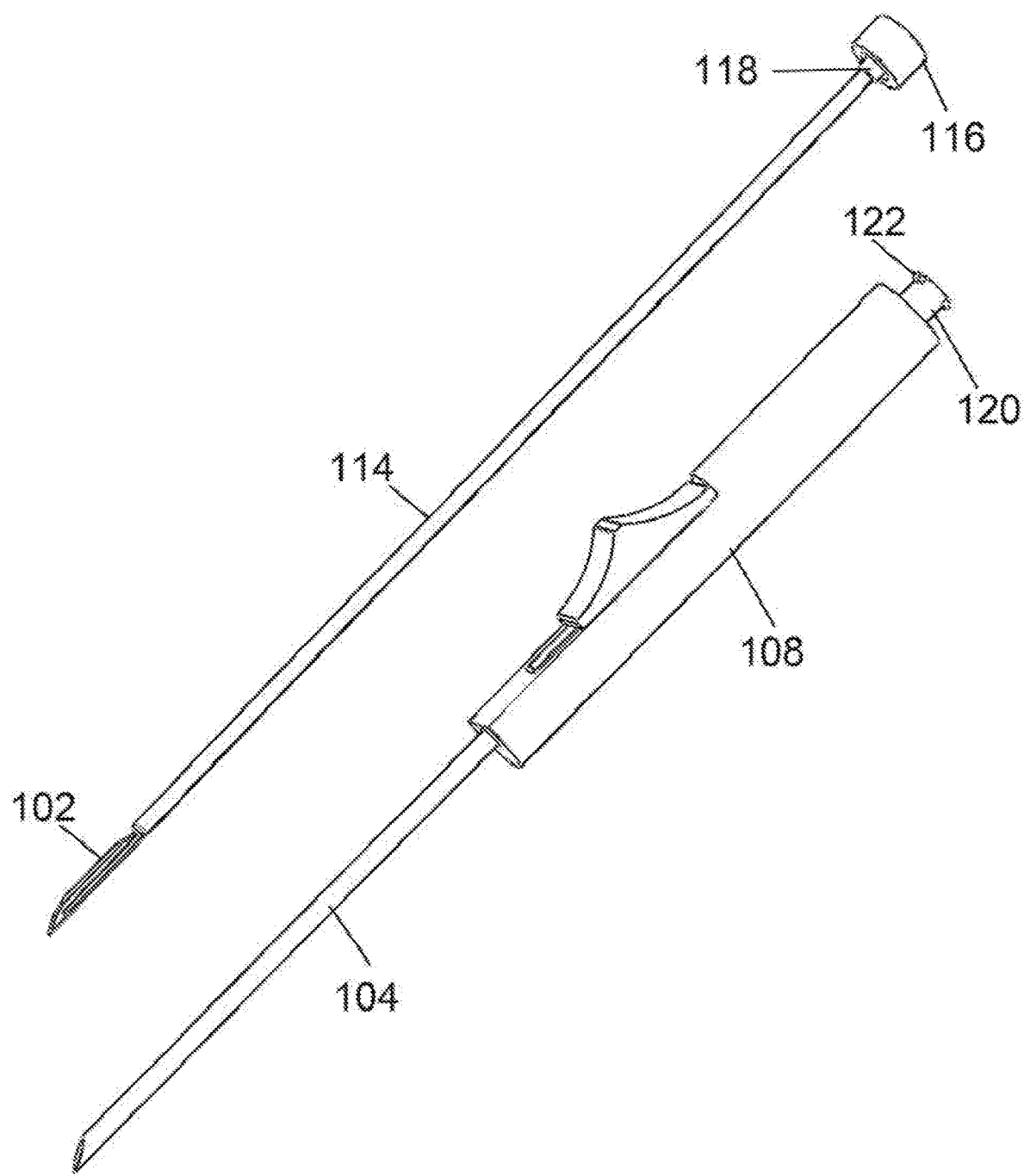
FIG. 3 is a perspective view of the needle-knife device of FIG. 1 with a stylet/cutting element/hub assembly removed from a needle/housing assembly.

Referring now to FIG. 3, the stylet 114 is shown completely removed from the housing 108. At the proximal end of the stylet 114, a hub 116 is shown fixedly attached. This hub 116 contains features which allows the hub to be removably attached to the housing 108. In this exemplary embodiment, the hub 116 utilizes an internal thread with a male luer 118. This male luer mates to a boss 120 on the housing 108 containing a female luer and external threads 122. Other attachment means may be employed such as snaps, however the use of standard luer fittings has the added benefit of allowing the attachment of syringes and other medical apparatus for other purposes. The stylet remains attached to the housing during normal operation. At points in the medical procedure it may become necessary to remove the stylet so as to place a guide pin through the lumen of the needle or inject fluids to the surgical site. The stylet is simply removed by twisting the hub 116 and pulling it (and stylet) away from the housing 108. In embodiments an internal seal such as an O-ring may be used to create a fluid-tight seal between the internal surface of the housing 108 and the external surface of the needle 104 in order to prevent injectable fluids like drugs from escaping the device.

In another embodiment of the stylet, the hub 116 may be configured on its proximal end to accept an electrosurgical connector. This would give the distal end of the stylet/cutting element capability to cut, coagulate, seal, desiccate, or fulgurate tissue with the use of an electrosurgical generator. Further details are provided in embodiments described later in this application.

Figure 4:
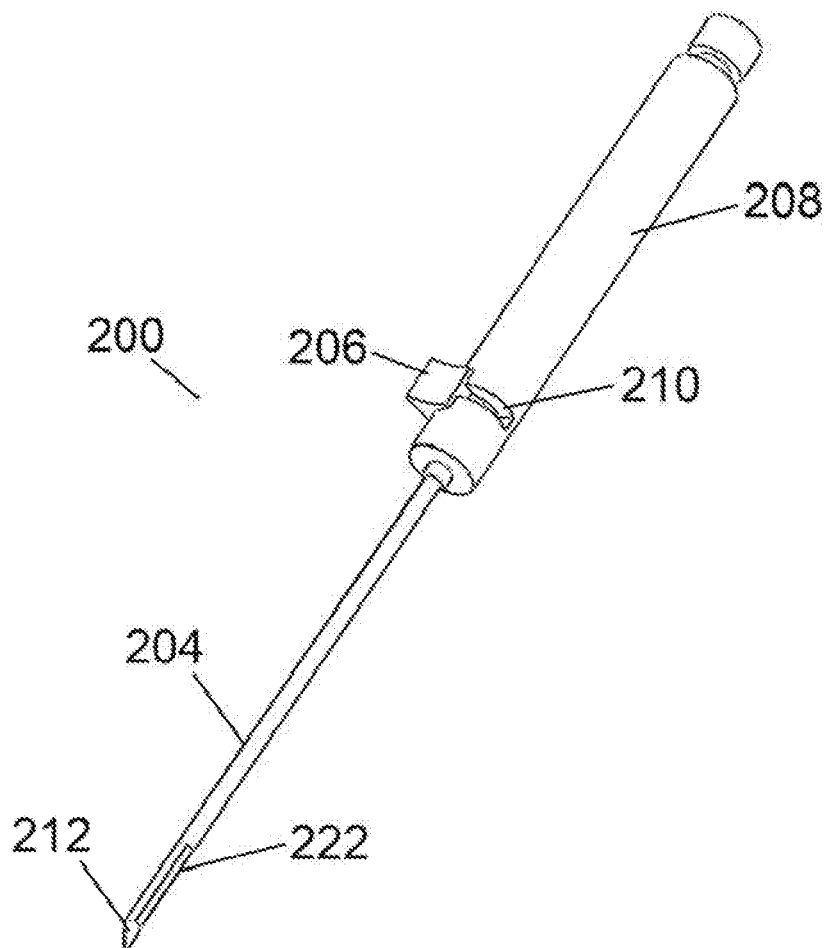
FIG. 4 is a perspective view another embodiment of a needle-knife device with windows in a needle and inner tube to expose a cutting element.

FIG. 4 shows another embodiment of a needle-knife device 200 which utilizes a window 222 in a penetrating needle 204 situated just proximal to the distal needle tip 212. A rotator knob 206 attached to the proximal end of the penetrating needle 204 and rides within a circumferential slot 210 in the housing 208 and facilitates rotation of the needle to align the window opening 222 with the cutting element 202 (shown in FIG. 5) so as to expose the cutting element. This view shows the window in the "closed" position, wherein the back side (opposite the cutting element) of the stylet obscures the window opening 222. The stylet of this embodiment is designed such that its outer diameter is very close to the inner diameter of the needle, creating a flush closure of the needle window. In other embodiments, a twist knob attached to the needle 204 and axially aligned and rotatably connected to the housing may facilitate rotation of the needle. Alternatively, the stylet 214 may be rotatable within the needle 204. In embodiments, another inner tube situated coaxially and rotatably within the needle and having its own window may be utilized to cover and expose the underlying cutting element.

Figure 5:
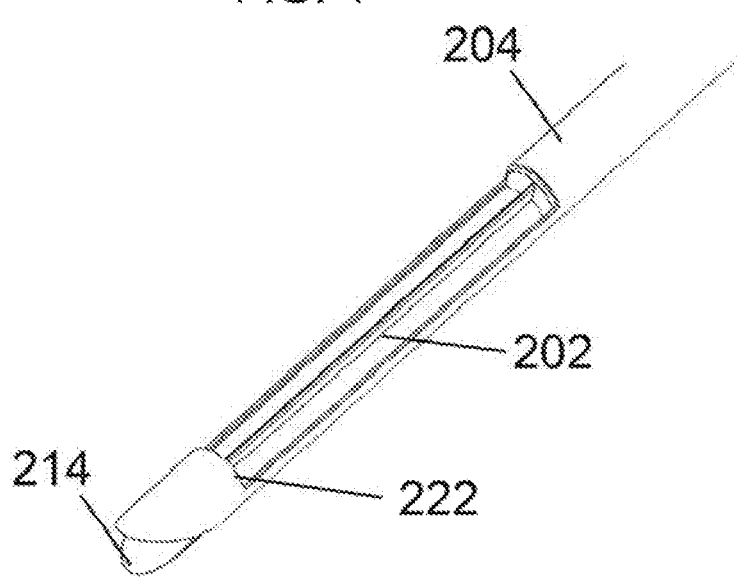
FIG. 5 is a close up view of the distal portion of the embodiment of FIG. 4.

FIG. 5 is a close up view of the distal end of the window needle-knife device of FIG. 4. Coaxially and rotatably situated within the penetrating needle 204 is a stylet 214 with cutting element 202. In this view the needle is shown rotated 180 degrees from its position in FIG. 4, which aligns the window 222 to expose the underlying cutting element 202. The stylet 214 can be rotated so that the cutting element 202 is exposed through the window 222 or not. With the underlying cutting element 202 exposed, tissue may be incised as in the other embodiments via manipulation of the entire assembly.

Figures 6, 7:
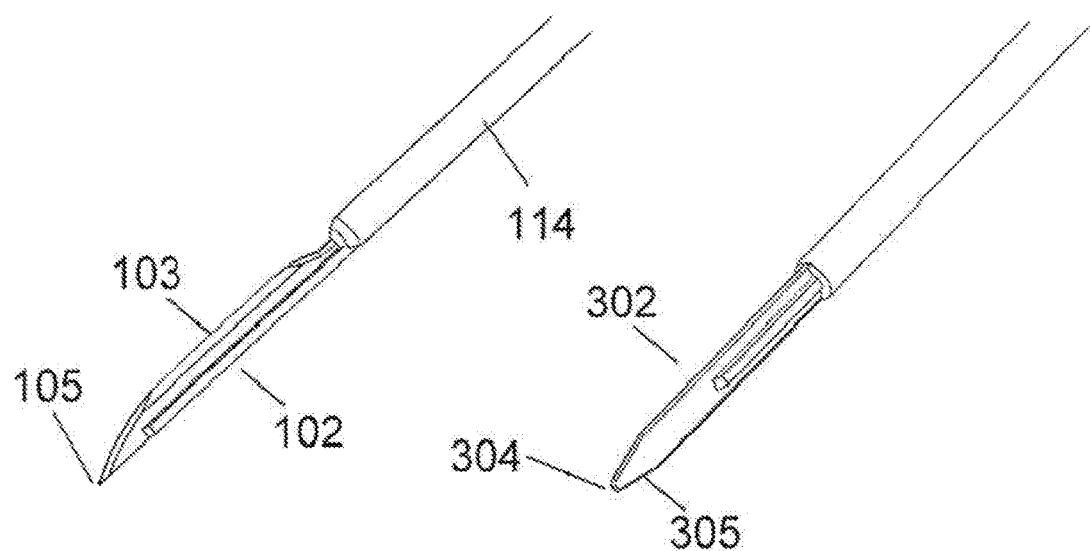
FIG. 6 is a perspective view of a cutting element for a needle-knife device in accordance with embodiments.
FIG. 7 is a perspective view of another embodiment of a cutting element for a needle-knife device, with the cutting element having dual cutting edges.

The cutting element 102 and/or 202 may generally be any sharp blade configuration, and can be straight, curved, angled and/or serrated. The cutting element 202 extends orthogonally from the axis of the stylet 214. FIG. 6 shows an embodiment of the cutting element 102 as used with the needle-knife embodiment of FIGS. 1-3. This cutting element is similar to a sharp pointed scalpel blade. The primary cutting edge 103 of the blade is positioned orthogonally to the axis of the stylet 114. The sharp point 105 may provide added utility in piercing tissue structures. Multiple cutting elements may be positioned side-by-side in the orientation shown here to provide additional cutting capability. In such a side-by-side arrangement, the cutting elements may be powered from an internal or external source so as to alternately reciprocate, thus providing enhanced cutting capability in certain media. In all embodiments, the cutting element (s) may be a separate component(s) that is affixed to the stylet or the cutting element and the stylet may be fabricated from a single piece of steel or other suitable material. All cutting elements disclosed herein may be utilized with either the open end needle-knife embodiments (e.g., FIG. 3) or the window needle-knife embodiments (e.g., FIG. 5).

FIG. 7 shows another embodiment of a cutting element 302 with a rounded tip 304. The cutting edge of the member is continued around the tip to create at least a partial cutting edge 305 on the back side of the blade. This may provide the added utility of cutting in the opposite direction without having to rotate the device 180 degrees. It is understood that a sharp tip may be combined with a double-edged cutting element just as a rounded tip may have only one sharp cutting surface.

Figures 8, 9:
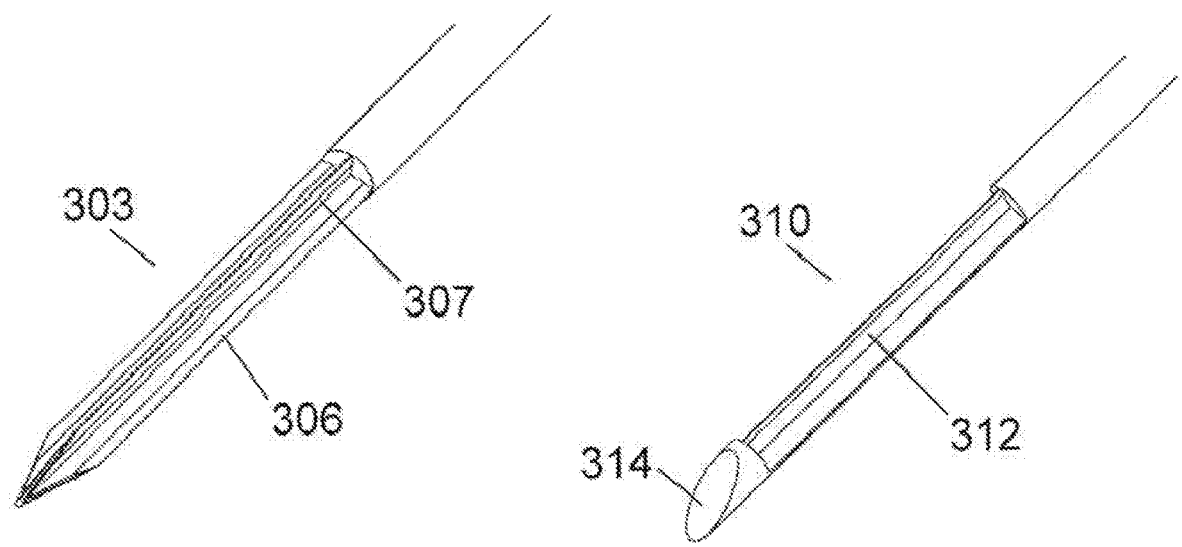
FIG. 8 is a perspective view of yet another embodiment of a cutting element for a needle-knife device, with the cutting element having a cruciform multi-cutting edge configuration.
FIG. 9 is a perspective view of still another embodiment of a cutting element for a needle-knife device, with a cutting element having a lumen-occluding element at the distal end.

FIG. 8 shows another embodiment of a cutting element 303 with a cruciform blade configuration. This configuration has a flat blade 306 with a second flat blade 307 crossing it in the center at 90 degrees. This type of blade arrangement may provide advantages for penetrating a tissue structure.

The embodiments of FIGS. 6-8 show cutting elements that do not occlude the lumen of the penetrating needle. In alternate embodiments, it may be advantageous for the tip of a cutting member to occlude the lumen of the penetrating needle so as to prevent tissue from clogging the needle lumen. For example, FIG. 9 is an embodiment of a cutting element 310 that has a flat surface 314 at the distal end of the cutting element 312. This flat surface 314 is shaped and angled so as to match the bevel of the outer needle. In embodiments, multiple cutting elements, such as the cutting element 312, may be arranged side-by-side behind the flat surface 314 so as to make multiple incisions simultaneously in tissue. Additionally, in the embodiment shown in FIG. 9, the surface 314 which occludes the lumen of the penetrating needle is flat, however in other embodiments the surface may take other shapes, such as rounded, bullet-shaped or pointed.

Figure 10:
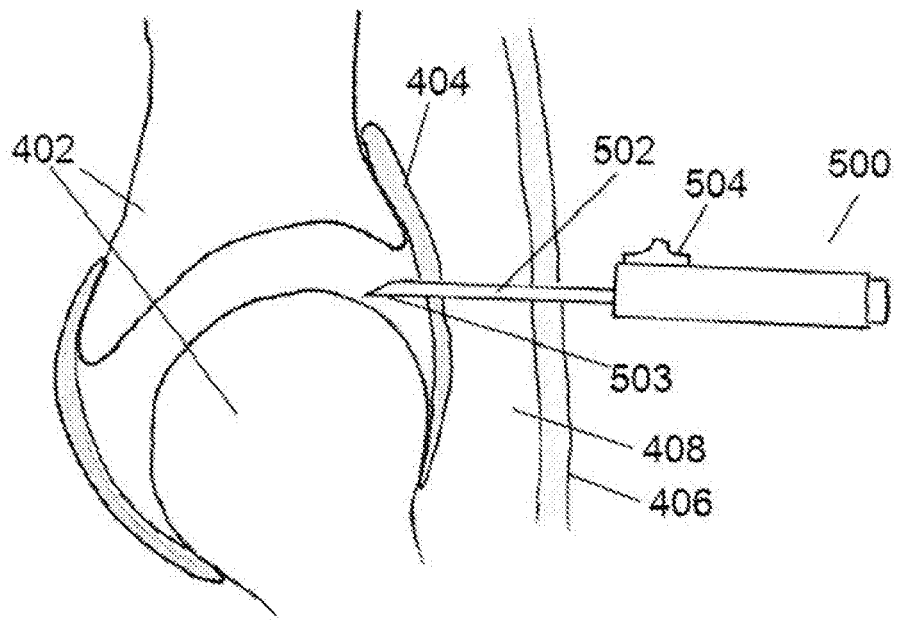
FIG. 10 is a diagrammatic representation of a partial section view of a human joint structure with a needle-knife device being used to create a capsulotomy in the human joint structure with a needle in a neutral state in accordance with embodiments.

Turning now to FIG. 10, a needle-knife device 500 is shown which may be used to create a capsulotomy in joint tissue. The needle-knife device may be substantially the same as any of the embodiments previously disclosed herein. In FIG. 10, a body joint is shown in cross section. The two bones 402 comprising the joint are shown, with a fibrous joint capsule 404 present. A skin layer 406 is represented with other soft tissue 408 residing between the joint capsule and the skin. The penetrating needle 502 of the needle-knife device 500 is shown penetrating through the skin layer 406, the other soft tissue 408, and into the joint capsule 404 such that the distal needle tip 503 is positioned just inside the joint capsule 404. The slider 504 on the device 500 is in its distal most position. In use, appropriate positioning of the needle in the joint space would be confirmed at this point by the user with endoscopic visualization or fluoroscopy or some other visualization system.

Figure 11:
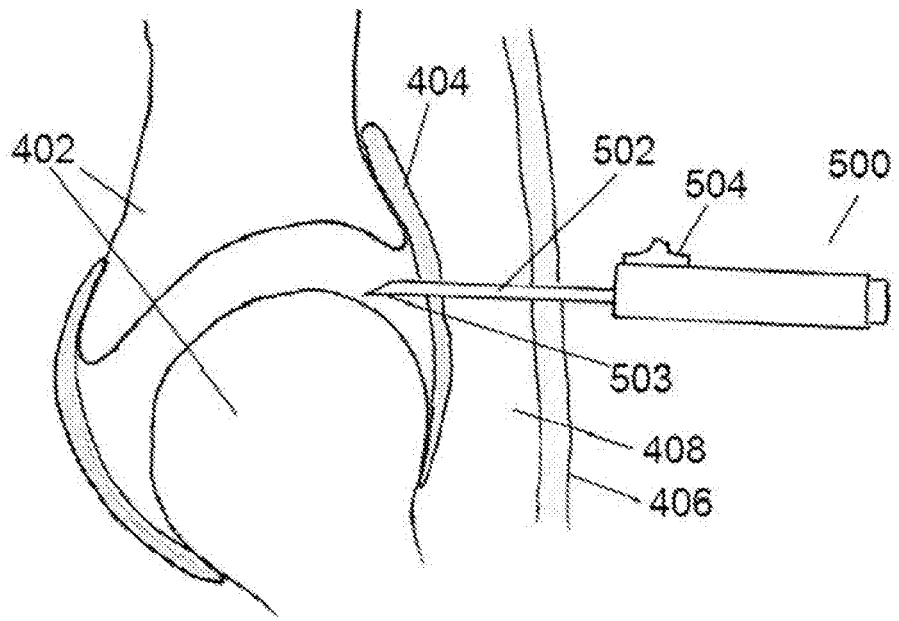
FIG. 11 is a diagrammatic representation of a partial section view of the human joint structure of FIG. 10, with the needle-knife device of FIG. 10, being used to create a capsulotomy in the human joint structure with the needle in a retracted position in accordance with embodiments.

FIG. 11 shows a further step in the capsulotomy sequence of the same joint space as FIG. 10. After insertion of the penetrating needle 502 into the joint capsule 404, the penetrating needle 502 may be retracted by moving the slider 504 toward the proximal end of the handle. By retracting the needle 502, the cutting element 506 is, exposed, residing in the same position in the joint that the needle tip 503 previously resided. At this point, the device may be manipulated so as to force the cutting element laterally to cut joint capsule tissue, thereby enlarging the incision in the capsule and creating space for the placement and maneuvering of subsequent instruments. Once the cutting is completed, the slider may be advanced distally to its original position, thus resheathing the cutting element for atraumatic withdrawal.

FIGS. 10 and 11 are intended as generic representations of a typical joint structure and may represent the shoulder joint, elbow, knee, or hip joints. Other joint structures such as the spine may also benefit from the similar use of the needle-knife device disclosed herein.

Figure 12:
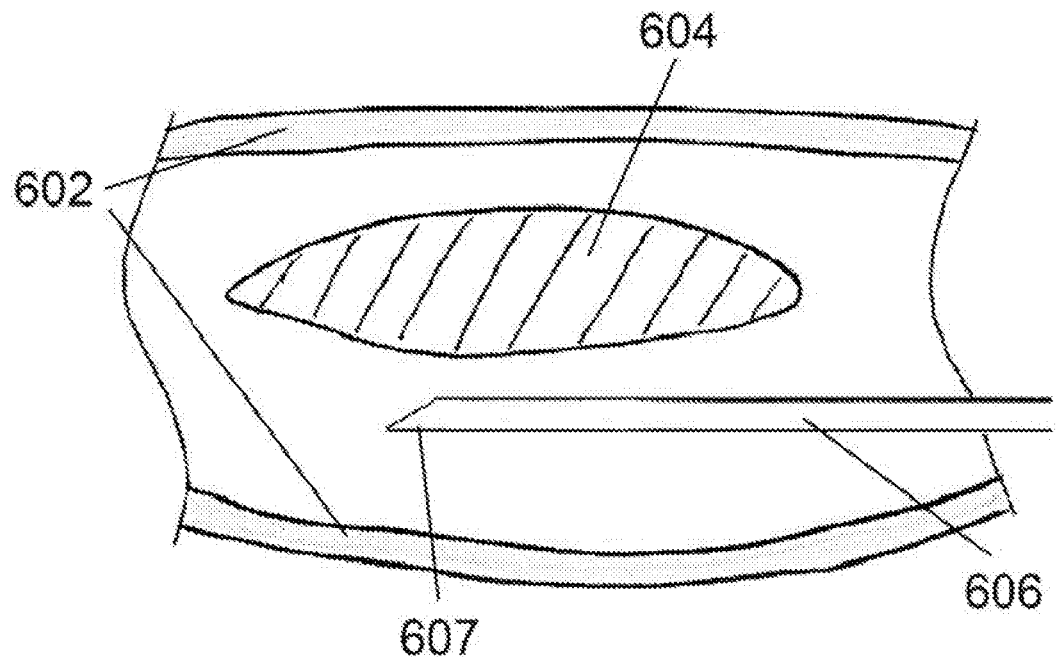
FIG. 12 is a diagrammatic representation of a partial section view of a body structure, with a needle-knife device being used to incise a ligament or fibrous tissue band in the body structure in accordance with embodiments.
Figure 13:
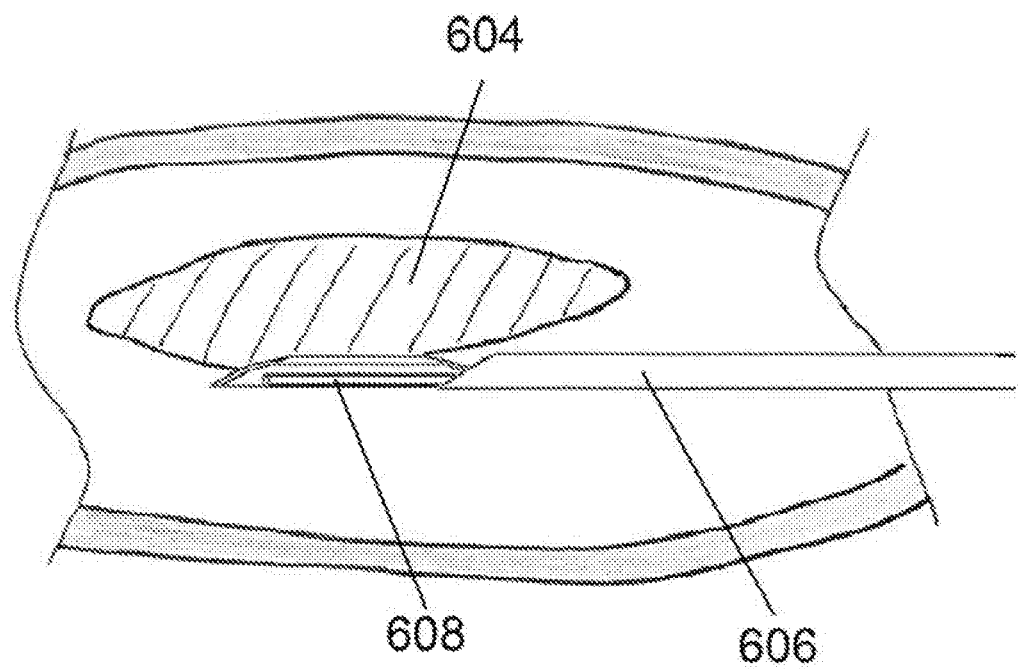
FIG. 13 is a diagrammatic representation of a partial section view of a body structure, with a needle-knife device being used to incise a ligament or fibrous tissue band in the body structure in accordance with embodiments.

FIGS. 12 and 13 are simplified generic representations of a body structure shown in cross section. This body structure could represent a hand or foot, leg or arm. The body structure has fibrous band or ligament 604 (shown in section) running through it below the skin level at 602. These figures show how a needle-knife device substantially the same as disclosed herein may be used to incise a fibrous band or ligament structure for medical purposes as may be done in "release" or other procedures. Typical procedures of this type include, but are not limited to plantar fascia release, carpal tunnel release, Achilles lengthening, illeotibial band release and compartment release.

FIG. 12 shows the penetrating needle 606 of said needle-knife device having been penetrated into the anatomical space surrounding a fibrous band or ligament 604. Ideally the needle 606 may be placed across the breadth of the band/ligament 604 such that the tip 607 is positioned under the distal side of the band/ligament 604. The needle 606 may then be retracted a specified distance as described previously, thus exposing the cutting element 608 as shown in FIG. 13. By manipulating the needle-knife device so as to push the cutting member 608 into and across the band/ligament 604, the band ligament is incised. A single incision with the cutting member may be sufficient, or depending upon the surgical procedure, multiple passes of the cutting member may be required to sufficiently incise the tissue. Any of the embodiments of the invention disclosed herein may be used for this type of medical procedure.

Surgical applications discussed thus far have been generally orthopedic in nature, however the scope of use of embodiments herein is not limited to only to orthopedics. Any surgical procedure requiring incision or modification of an internal tissue structure may benefit from the use of the needle knife device. Particularly, the needle-knife device can be particularly useful in minimally invasive procedures where a secondary visualization source (e.g. scope camera, x-ray, or ultrasound) is used. Examples of other procedures may include, but are not limited to, cardiac surgery, neurosurgery, gynecological, gastrointestinal or general laparoscopic surgery. Variations on the embodiments disclosed herein may enhance the usefulness for specific surgical applications. For example, the typical length of the needle of the embodiments disclosed herein for arthroscopic procedures might be in the range of 0.5 to 5 inches (except for hip arthroscopy which is about 8 inches). However, for general laparoscopic surgery, a significantly longer needle may be useful (6-14 inches) in order to reach the surgical site.

Further, depending on the visualization method used for the surgical procedure, variations of the embodiments disclosed herein may enhance visualization of the device. For example, certain surface modifications, treatments, or coatings may be applied to the needle, blade and/or stylet to enhance their visibility when used with ultrasound guidance. Such treatments may include but are not limited to dimpling, blasting and coating so as to alter the component's interaction with the ultrasound waves, making it more readily visible.

Up to this point embodiments disclosed herein have focused on a cutting stylet within the needle structure. Further embodiments include a stylet configured at the distal end to perform functions other than cutting, as with a sharp blade. Such functions may include but are not limited to scraping, gouging, debriding, fenestrating, roughening, skiving, filing, or sanding. Said functions may generally be employed in an effort to remodel the tissue for clinical benefit. The stylet of the present invention may be configured to perform any one or more of these tasks, and may further be removable as previously disclosed. This removability lends itself to creation of a system, wherein different stylets with different configurations and different functions may be inserted into the needle to perform a more complex task and interchanged with other stylets to perform a new task as the clinical situation may dictate. This interchanging may be accomplished without ever moving the needle from a specific anatomical site.

Figure 14:
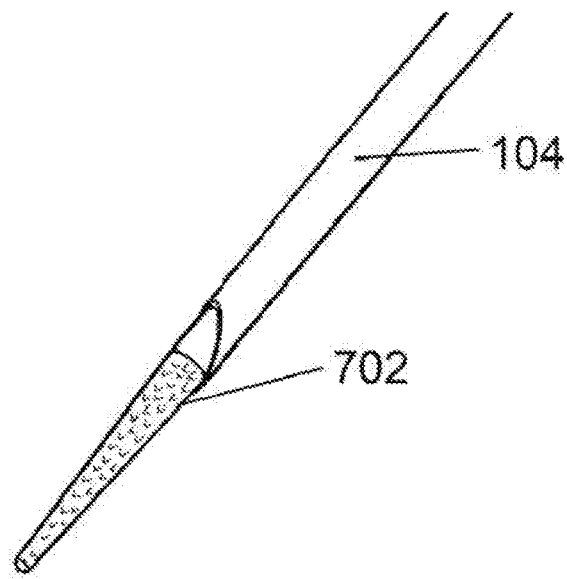
FIG. 14 is a perspective view of a distal end of a needle knife device having a conical stylet configured for tissue remodeling.
Figure 15:
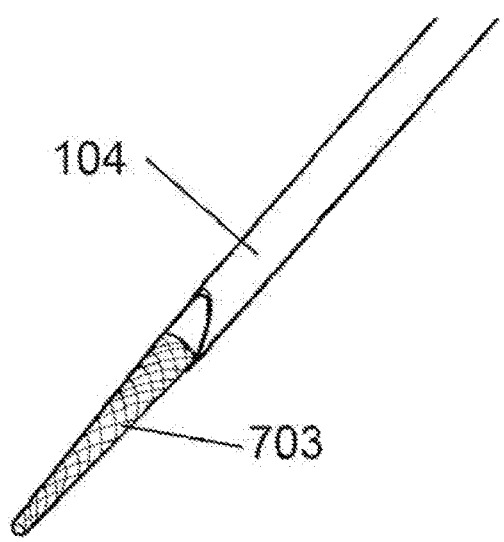
FIG. 15 is a perspective view of a distal end of another embodiment of a needle knife device having a stylet configured for tissue remodeling.

Turning back to the figures, FIG. 14 shows an embodiment similar in structure to prior embodiments with a penetrating needle 104 and removable stylet 702. The distal tip of the stylet 702 is a conical shape and has a roughened surface. FIG. 15 shows a similar configuration, but the stylet has a knurled surface 703. The stylets 702 and 703 with the roughened surfaces can be used for debriding of bone or other hard tissue so as to remodel the tissue structure. As with prior embodiments, the conical roughened tip may reside behind the cutting edge of the needle during needle penetration, then exposed as the needle is retracted in preparation for tissue remodeling. The stylet/assembly may then be rotated or reciprocated so as to remodel the tissue. While the distal portion of the stylet of these embodiments is shown in a conical, tapered configuration, other embodiments have a straight, non-tapered tip or a reverse-tapered tip.

Figure 16:
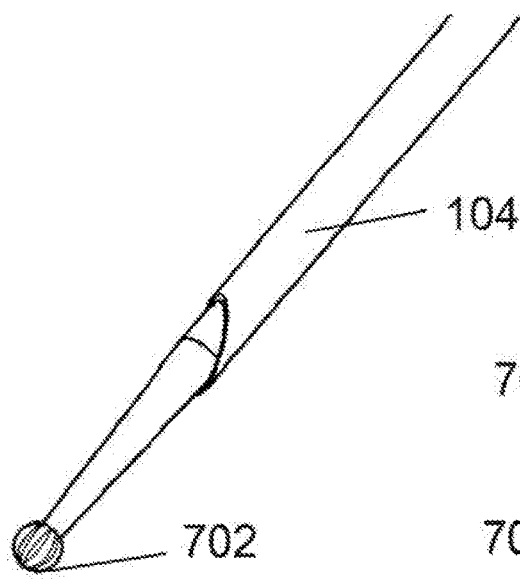
FIG. 16 is a perspective view of a distal end of another embodiment of a needle knife device having a spherical-tipped stylet configured for tissue remodeling.

FIG. 16 shows a similar embodiment wherein the distal stylet tip is spherical in shape and contains cuts 704, such as indentations or grooves, in a spiral formation about the spherical stylet tip. With such a configuration, the stylet may be rotated either manually or by a powered source so as to remove small amounts of surface tissue (i.e., via the cuts 704) in an effort to remodel the tissue.

Figure 17:
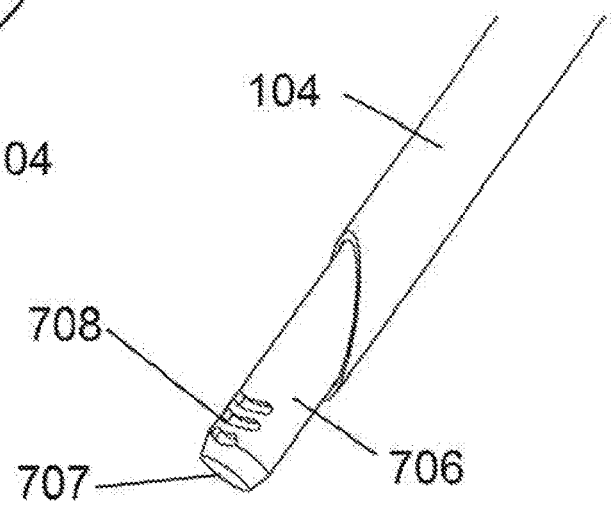
FIG. 17 is a perspective view of a distal end of another embodiment of a needle knife device having tubular stylet configured for tissue remodeling.

A stylet may also be composed of a tubular member 706 with an open end 707 as shown in FIG. 17. Such a stylet may be used to gouge or scrape bone or other hard tissue so as to remodel the tissue. With a tubular stylet as disclosed herein, a suction source may be attached at the proximal end and suction applied through the tube to remove small pieces of loose tissue debris as it is released from the main body of tissue. Additionally, openings 708 in the sidewall of the tubular stylet may allow for debriding or scraping of bone or tissue at an alternate angle of approach.

Figure 18:
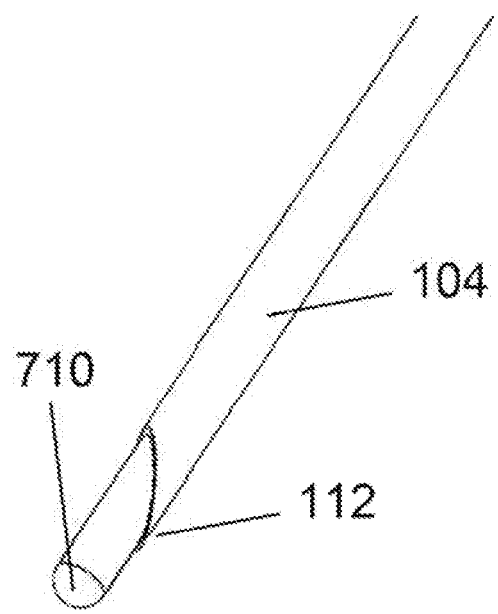
FIG. 18 is a perspective view of a distal end of another embodiment of a needle knife device having a rounded tip blunt stylet configured for blunt tissue dissection.

In some situations it may be desirable to have a stylet tip that may simply act as a blunt tissue dissector. FIG. 18 shows an embodiment of a device with such a blunt, rounded stylet tip 710. In this embodiment the rounded stylet tip may reside beyond the distal tip 112 of the penetrating needle 104 so as to provide blunt dissection only. At any point during the clinical procedure, the rounded tip stylet 712 may be removed and replaced with other stylets as disclosed herein to perform alternate functions as the procedure or the patient anatomy may demand.

Figure 19:
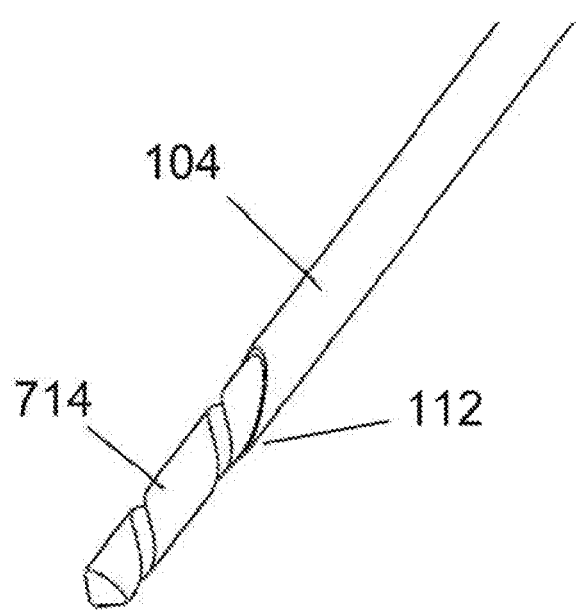
FIG. 19 is a perspective view of a distal end of another embodiment of a needle knife device having a drill-bit stylet configured for drilling holes in tissue.

In some clinical situations, it may be desired to drill holes in the bone, as in the case of treating lateral epicondylitis in the elbow. FIG. 19 shows an embodiment of the device with a stylet 714 that is configured as a drill bit. When the needle 104 is retracted, the drill bit portion of the stylet is exposed beyond the distal tip 112 of the needle and a hole may be drilled in the tissue by rotating the stylet from the proximal end. As in previous embodiments, the stylet may be rotated manually or attached to a powered driver source.

Figure 20:
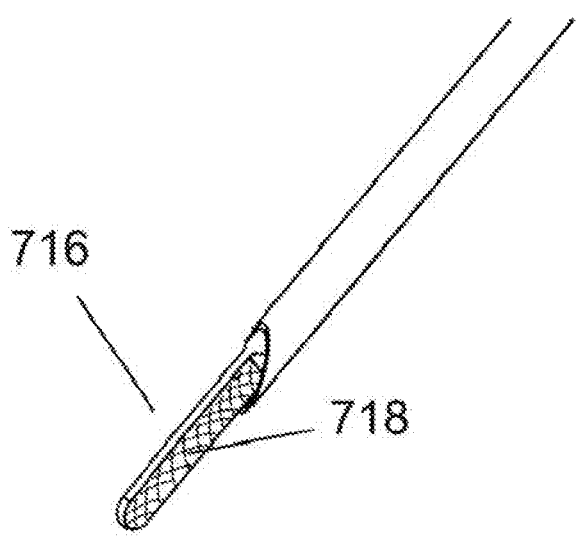
FIG. 20 is a perspective view of a distal end of another embodiment of a needle knife device having a flat-sided stylet configured for tissue remodeling.

FIG. 20 shows another embodiment wherein the distal stylet tip 716 has flat sides. The flat sides have a knurled or roughened surface 718 that can be used to remodel the tissue as necessary for the clinical situation. The distal tip 716 may have one or multiple flat surfaces.

Figure 21:
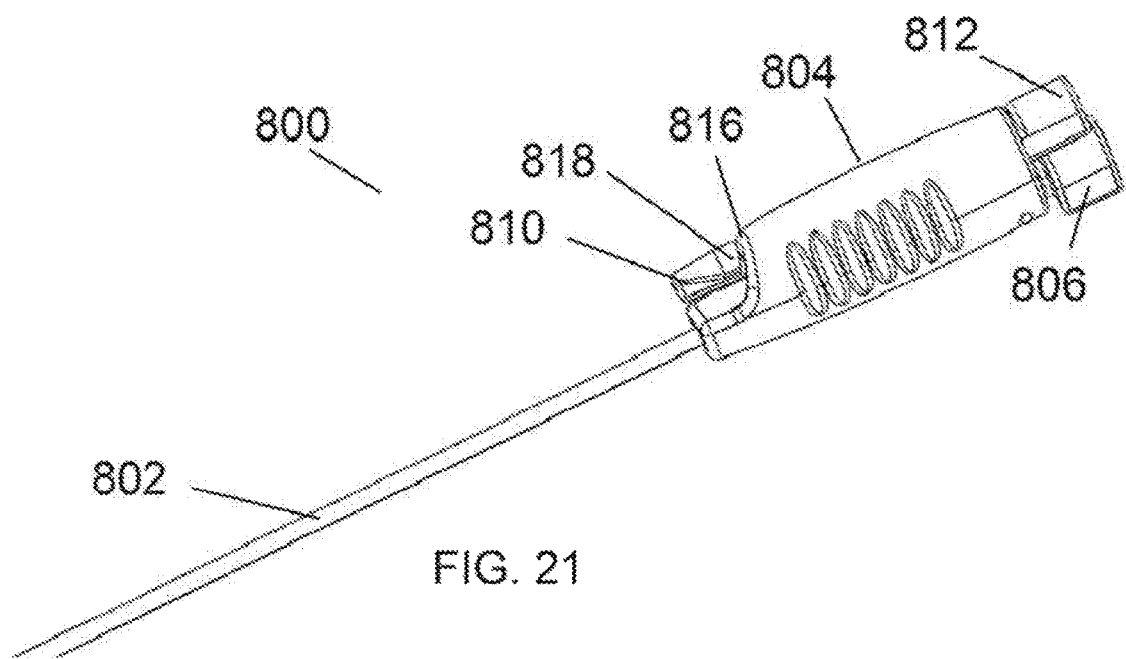
FIG. 21 is a perspective view of an embodiment of a needle knife device having an automatically retracting needle with a small handle for fingertip control.
Figure 22:
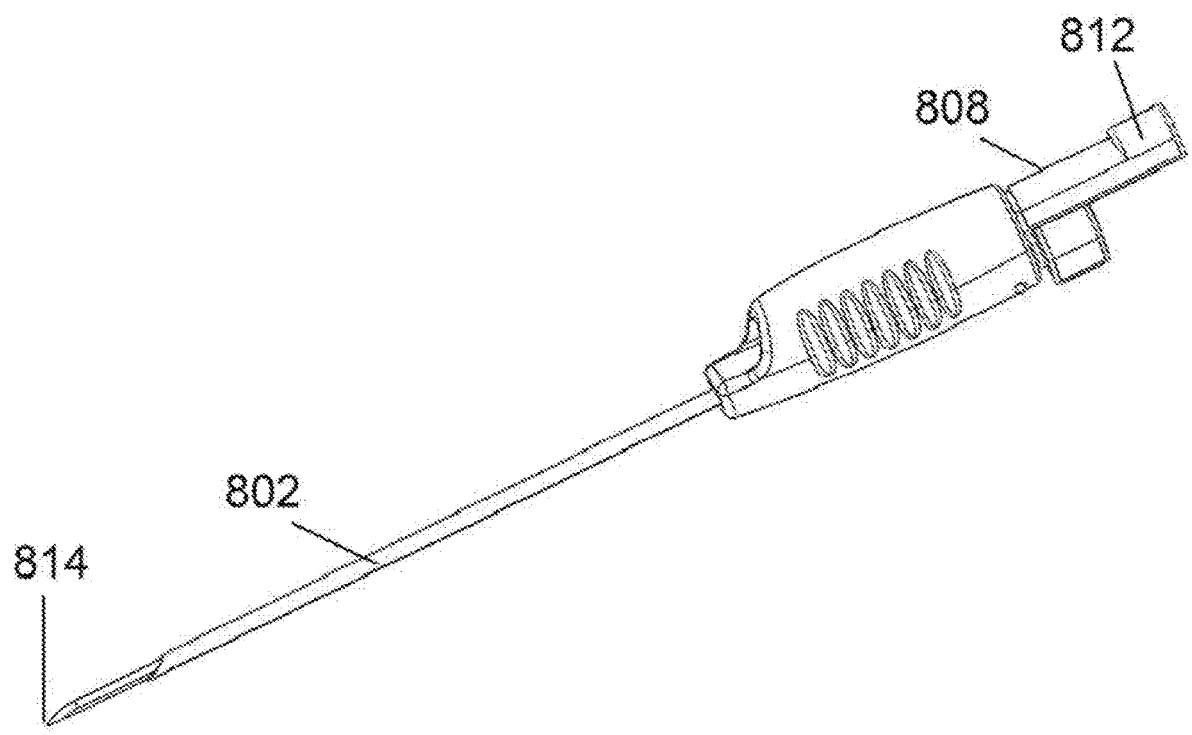
FIG. 22 is a perspective view of the needle knife device of FIG. 21 shown with a needle retracted.
Figure 23:
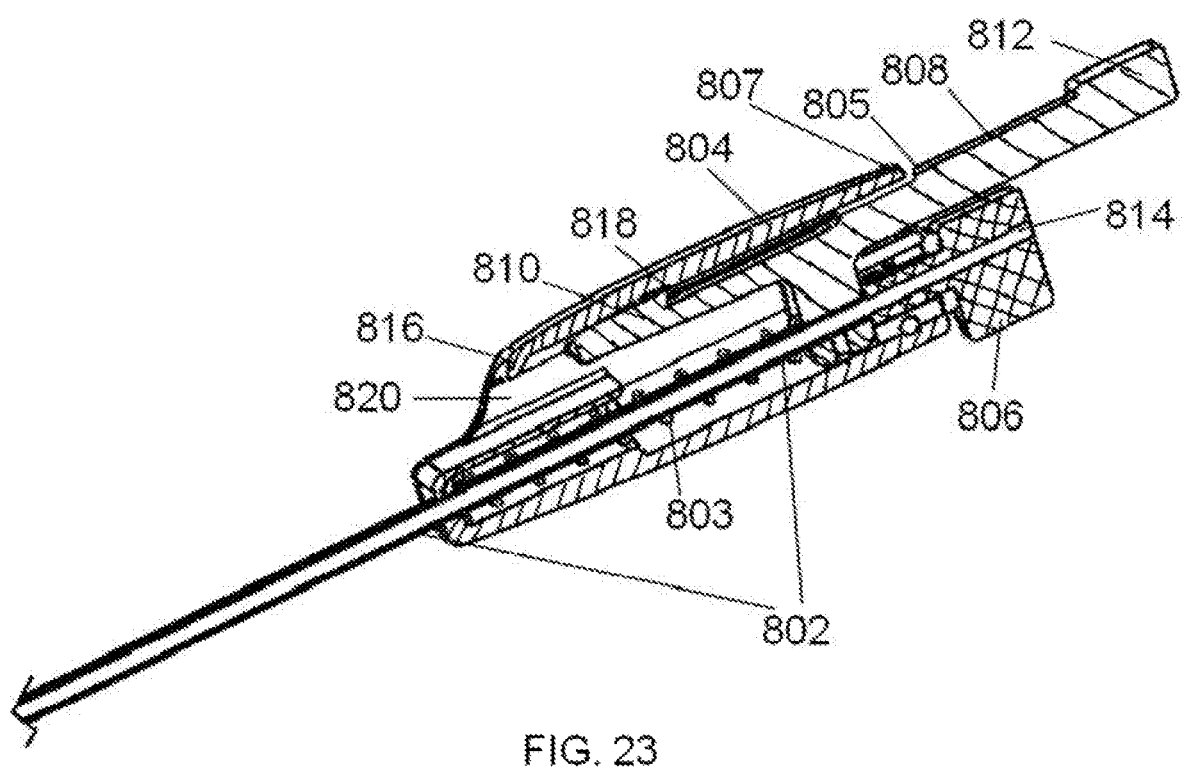
FIG. 23 is a magnified cross section view of the needle knife device of FIGS. 21 and 22.

Prior embodiments of the proximal end of the device disclosed herein show a housing or hand piece designed to be gripped in the palm or by a majority of the hand as is typical of many surgical hand pieces. FIG. 21 is an embodiment of a needle-knife device 800 with a smaller housing 804 at the proximal end that is designed to be held and manipulated with the fingertips. As with prior embodiments, a penetrating needle 802 is present and shown in the extended position with a bladed stylet disposed inside the needle lumen. The stylet is fixedly attached at the proximal end to a hub 806. The stylet/hub assembly is removable and replaceable with other stylets of similar form and in a manner as disclosed in prior embodiments. The penetrating needle 802 is fixedly attached to a shuttle 808 (FIG. 22). This shuttle 808 is slidably disposed within the housing 804 so as to move the penetrating needle in the axial directions. The shuttle 808 of this embodiment has a distal tip 810 and a proximal tip 812 (FIG. 23). A compression spring 803 is utilized to retract the penetrating needle 802 and expose the cutting blade or other structure at the distal end of the stylet. The intent is to provide needle retraction with a very limited finger movement, as in pushing a button with a fingertip. In a latched position, the shuttle 808 is pressed distally, against the bias of the spring 803, until a back edge 818 of the distal shuttle end 810 latches behind a front edge 816 of the housing 804. The internal compression spring 803 applies a force in the proximal direction against the shuttle 808 so that when the distal tip 810 of the shuttle is pushed inward toward the needle by a technician's finger, the shuttle "unlatches" and is free to move proximally under the force of the compression spring.

FIG. 22 shows the same device 800 with the penetrating needle 802 in the retracted state so as to expose a cutting blade 814. The proximal tip 812 of the shuttle 808 is shown in displaced position as forced there by the compression spring.

In FIG. 23, the compression spring 803 is shown within the housing at full extension and pushing the shuttle 808 to its proximal position. The penetrating needle 802 is shown fixedly attached to the shuttle 808, such that movement of the shuttle in the axial direction produces retraction and extension of the needle 802 relative to the stylet with cutting blade 814.

The proximal end of the stylet with cutting blade 814 is fixedly attached to the hub 806. When the proximal tip 812 of the shuttle 808 is pushed distally by the operator, the shuttle 808 with attached penetrating needle 802 moves axially forward within the housing 804 and compresses the spring 803 until a back edge 818 of a distal tip 810 of the shuttle catches on the front edge 816 of an opening 820 in the housing 804. At this point, the spring 803 is compressed and the penetrating needle 802 is extended forward so as to cover the cutting blade, putting the mechanism into a "cocked" state. When the operator wishes to retract the needle 802 to expose the cutting blade, the distal tip 810 of the shuttle 808 is pressed inward toward the needle, thus dissociating the back edge 818 of the shuttle from the front edge 816 of the opening 820 in the housing 804. This allows the spring force to push the shuttle 808 and associated needle 802 proximally to uncover the cutting blade. A front edge 805 of the proximal shuttle end 812 catches on a back edge 807 of the housing 804 preventing forward movement of the needle. This may be of particular use when friction created by skin and other tissue around the needle is great enough so as dislodge the needle inadvertently.

Figure 24:
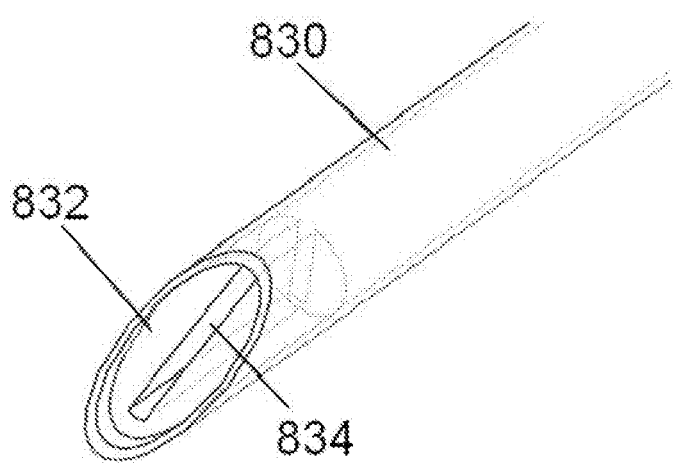
FIG. 24 is a hidden line perspective view of the distal tip of an embodiment of a needle knife device having a lumen-occluding element.

FIG. 24 is another embodiment wherein the penetrating needle 830 contains a lumen-occluding element 832 shown in partially hidden lines. The inclusion of a lumen-occluding element in the device may be necessary to prevent tissue from entering the lumen of the needle 830 upon penetration through the tissue. The lumen-occluding element 832 may have a slot 834 which allows extension of a cutting blade when the cutting needle 830 is retracted. The slot 834 may be rectangular, square, round, or any other shape that may be required to allow for passage of a cutting blade or other tissue-remodeling element. The lumen-occluding element is generally fixedly attached to the penetrating needle and may be very short like a wafer or may extend a significant distance down the lumen of the needle to the extent that it may extend the full length of the penetrating needle. The lumen-occluding element may be preferably manufactured from plastics or metals commonly used in medical devices. Other materials such as ceramics or foams may also be suitable.

Figure 25:
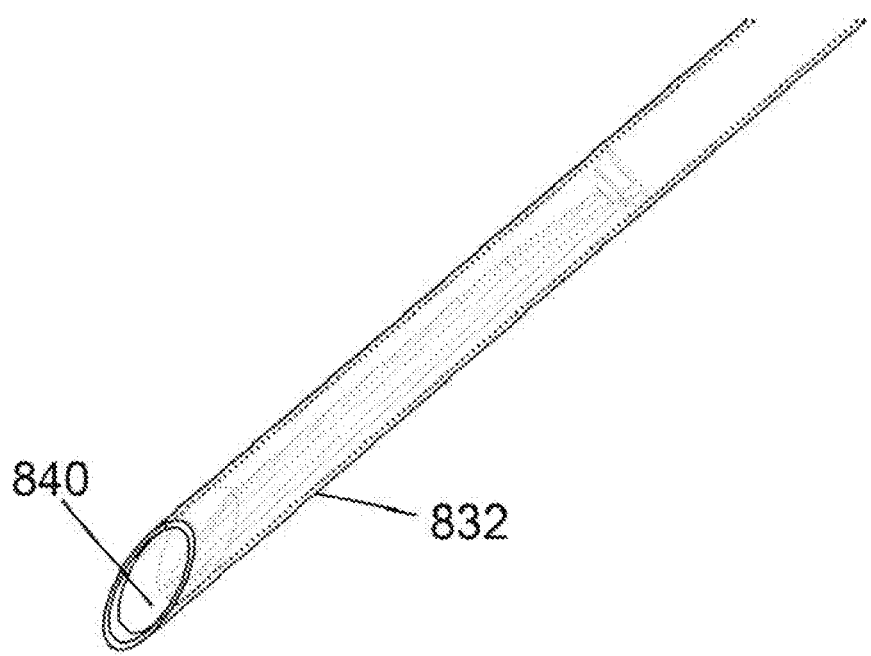
FIG. 25 is a hidden-line perspective view of a distal tip of an embodiment of a needle knife device having a lumen-occluding element integral with a stylet/cutting blade.
Figure 26:
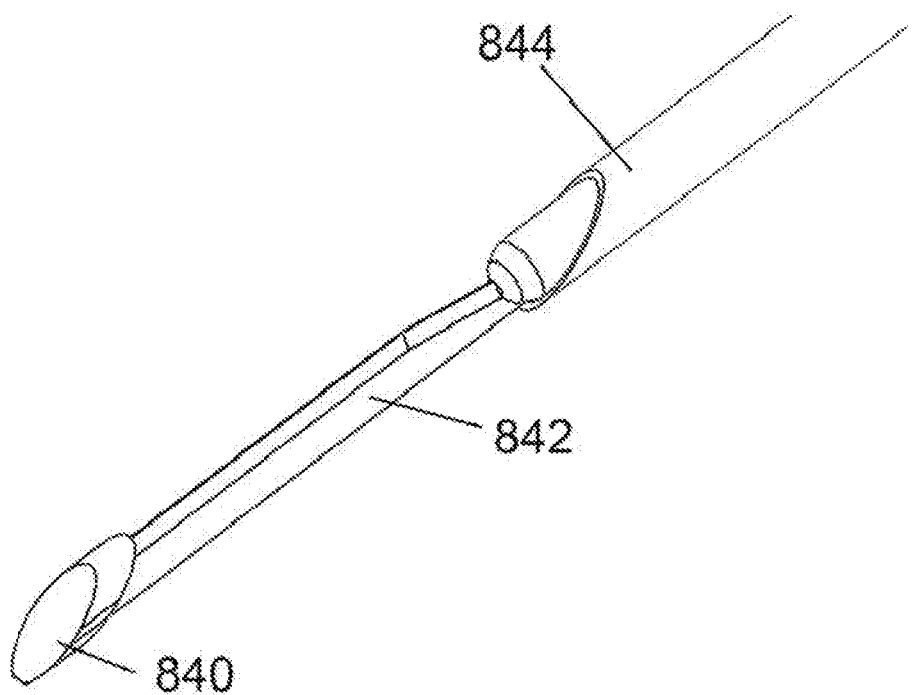
FIG. 26 is a perspective view of a distal tip of an embodiment of a needle knife device having a lumen-occluding element integral with a stylet/cutting blade with a needle in a retracted position.

A lumen-occluding element may also be integrated with the stylet/or cutting blade. FIGS. 25 and 26 illustrate such an embodiment. In FIG. 25, the lumen-occluding element 840 is integrated with the stylet/cutting blade 842 and is shown in hidden lines within the lumen of the penetrating needle 844. FIG. 26 shows the penetrating needle 844 retracted to expose the cutting blade 842 with a lumen-occluding element 840 at the distal tip. In this embodiment, the lumen-occluding element 840 is a disc-shaped element. In other embodiments, the lumen-occluding element may be any shape which partially or substantially occludes the lumen of the penetrating needle such as spherical or multi-faceted shapes such as rectangular or hexagonal. The lumen-occluding element is preferably manufactured from metals or plastics commonly used for medical devices. It may be formed integrally with the cutting blade from the same piece of raw material or may be fabricated separately and attached to the cutting blade via a friction fit, adhesive, snap fit, welding or other assembly mechanism.

FIGS. 27-29 show an embodiment of the present invention substantially the same as the embodiments of FIGS. 1-3, but refined for ease-of-use and manufacturability. Contours on the underside of the handle provide a place for the user's fingers to grip and strategically placed ridges 906 provide better traction for the user to manipulate the device. The slider 902 which manipulates the needle 908 is shown in the forward position thus covering the cutting blade 910. Also provided in FIGS. 27-29 is a locking feature which helps to prevent needle retraction when penetrating the skin or other tissues. A locking feature to prevent needle movement may take many forms. Shown here is a bayonet-style lock, wherein the slider 902, when advanced fully forward, is secondarily moved to the side (in an axial fashion) and into a slot which prevents backwards movement and subsequent retraction of the needle. In FIG. 27, the slider 902 is shown in the locked position and thus rests off-center from the rest of the handle.

FIG. 28 shows a front view of the device in the locked mode, where the slider 902 can be clearly seen in a position offset from the center of the handle. In use, the operator would manually move the slider 902 back to the center position and thus out of the locking slot prior to retracting the slider to subsequently retract the needle and expose the cutting blade.

FIG. 29 shows a partial cut-away view of the needle knife device with a locking mechanism. The slider and needle are shown in the "unlocked" and retracted position. In this embodiment, a biasing member 912 is shown which is designed to facilitate movement the slider 902 sideways into a locking slot as the use user pushes the slider forward to extend the needle 908 over the cutting blade 910. In embodiments, the biasing member may be a separate component that is attached to the handle or may be manufactured as parts of the handle itself. In yet other embodiments, no biasing mechanism may be present, thus requiring the user to manually push the slider 902 into the bayonet slot. Other mechanisms may be employed to prevent proximal movement of the needle and slider such as a button-like protrusion on the slider which protrudes through a hole or slot in the handle and must be actively disengaged by the user in order to allow movement of the slider and needle. Another example of such a mechanism would be a pull tab or break-away tab which provides a physical block preventing the slider from moving proximally and may be manually removed by the operator. Such locking mechanisms are designed with sufficient strength so as to prevent proximal needle movement when piercing the skin or other soft tissues.

Figure 30:
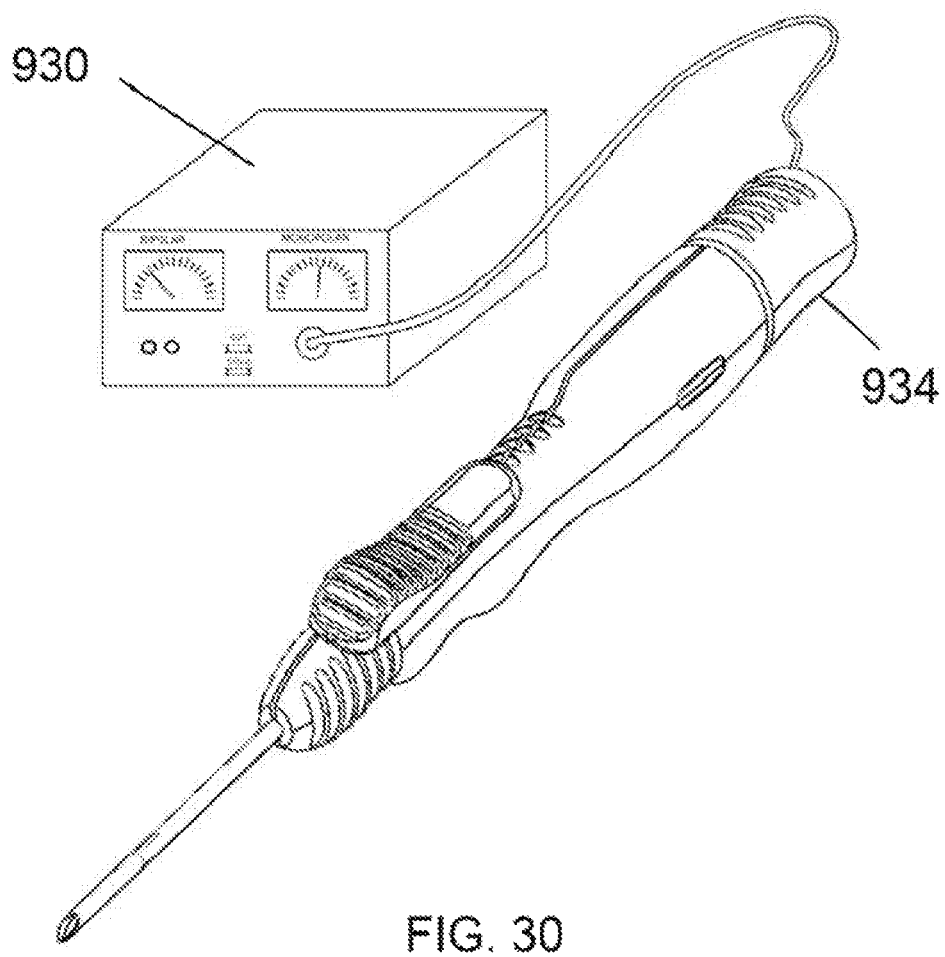
FIG. 30 is a perspective view of an embodiment of a needle knife device configured to connect to an electrosurgical generator.

As disclosed in prior embodiments, cutting and coagulation of certain tissues may be achieved or enhanced by application of energy though the blade/stylet and/or needle. One example of said energy would radiofrequency electrical energy or RF. Radiofrequency electrical energy is common in the surgical setting and RF generators are found in nearly all surgical suites. FIG. 30 shows an embodiment of the needle knife device configured for use with an RF generator 930. The needle knife device is configured with one or more standard RF receptacles (male or female) for connection to the RF generator 930. The plug is internally connected to the blade/stylet through the cap 934 such that electrical energy may be delivered to the cutting blade or other functional instrument at the end of the stylet. The use of electrical current with the device may require additional features for effectiveness such as insulation along the length of the stylet or needle so as to prevent dispersion of the current to surrounding tissues and concentrate it at the un-insulated distal tip. Any other design aspects typically found in electrosurgical instruments which enhance safety or effectiveness may be applied to the needle knife device in a similar manner. Other examples of energy that may be applied through the needle knife device include, but are not limited to, ultrasonic vibration and thermal energy.

In embodiments, the invention disclosed herein may be configured to work with nerve monitoring equipment. Certain procedures may be carried out in the vicinity of critical neurological structures (e.g. the ulnar nerve in the wrist/hand) making it important know the location of the tip of the needle knife device with respect to such a structure. In a similar manner as configured for electrical generation, the proximal end of the stylet may be configured to accept neural monitoring connections. Alternately, a specific stylet with a nerve-sensing probe at the distal tip may be inserted into the needle knife device as described herein and connected to nerve monitoring equipment. Once the proximity to the nerve is verified with said probe, that nerve-sensing stylet may be remove and replaced with a cutting stylet.

The needle-knife device shown in FIGS. 1-30, is preferably constructed using materials and methods typically used to construct handheld surgical instruments. Such materials for the hand piece may be but not limited to metals such as stainless steel or aluminum, or plastics such as ABS, polycarbonate, polyethylene, polysulfone, acetal or other suitable thermoplastics. The penetrating needle described herein may be constructed from suitable metals as a typical hypodermic needle. Stainless steel, nitinol or other metals may be appropriate. The cutting member of the invention disclosed herein is preferably stainless steel or carbon steel but other metals may be appropriate such as nitinol, or aluminum. Ceramics and plastics may even be utilized as to the extent of their ability to hold an appropriately sharp edge. The cutting member may have a smooth edge or may be serrated so as to better incise certain tissues. The elongated rod or stylet disclosed herein that connects the cutting member to the hub or housing may be made of any suitable metal or plastic. For example, if some flexibility or curvature were required over the length of the needle, then the needle and/or stylet may be composed of nitinol or other shape memory or flexible alloy so as to allow a greater degree of flexibility and/or curvature.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A minimally invasive method of incising an internal tissue of a patient, the method comprising:
   supporting a penetrating needle via a handle;
   supporting, via the handle, a cutting blade sheathed within a lumen of the penetrating needle;
   penetrating through skin and underlying tissue of a patient with a distal tip of the penetrating needle with the cutting blade sheathed within the lumen;

exposing the cutting blade by operating a mechanism that repositions the penetrating needle proximally relative to the handle and the patient or rotates the penetrating needle relative to the cutting blade; and manipulating the exposed cutting blade to incise an internal tissue of the patient.

2. The method of claim 1, comprising removing the cutting blade from the lumen via retraction through the lumen.

3. The method of claim 2, comprising injecting fluid through the lumen into the patient after the removal of the cutting blade from the lumen.

4. The method of claim 2, comprising placing a guide pin into the patient after the removal of the cutting blade from the lumen.

5. The method of claim 1, wherein the mechanism repositions the penetrating needle proximally relative to the handle and the patient by translating the penetrating needle proximally relative to the handle and the patient via extension of a compression spring operatively coupled between the penetrating needle and the handle.

6. The method of claim 1, wherein the mechanism rotates the penetrating needle relative to the cutting blade to align the cutting blade with an aperture in a side of the penetrating needle.

7. The method of claim 1, wherein the cutting blade is fixedly attached to an elongated member that extends through the lumen and is detachably attached to the handle.

8. The method of claim 7, wherein the elongated member comprises a stylet.

9. The method of claim 7, comprising occluding a distal end portion of the lumen with a distal end portion of the elongated member during the penetrating through skin and underlying tissue of the patient with the distal tip of the penetrating needle with the cutting blade sheathed within the lumen.

10. The method of claim 1, wherein the incised internal tissue is a joint capsule.

11. The method of claim 1, wherein the incised internal tissue is a bone, a ligament, or a fibrous band of tissue.

12. The method of claim 1, wherein the cutting blade extends orthogonally to a length axis of the penetrating needle during the incision of the internal tissue.

13. The method of claim 1, comprising monitoring, using ultrasound imaging, the penetrating through skin and underlying tissue of the patient with the distal tip of the penetrating needle with the cutting blade sheathed within the lumen.

14. The method of claim 1, wherein the mechanism comprises a slider that is slideably coupled with the handle for selective translation of the penetrating needle relative to the handle.

15. The method of claim 1, wherein the penetrating needle is fixedly attached to the mechanism comprises a rotator knob that is rotationally coupled with the handle for selective rotation of the penetrating needle relative to the handle.

16. A minimally invasive method of remodeling an internal tissue of a patient, the method comprising:

supporting a penetrating needle via a handle;

supporting, via the handle, a tissue remodeling member sheathed within a lumen of the penetrating needle penetrating through skin and underlying tissue of a patient with a distal tip of the penetrating needle with the tissue remodeling member sheathed within the lumen;

exposing the tissue remodeling member by operating a mechanism that repositions the penetrating needle proximally relative to the handle and the patient or rotates the penetrating needle relative to the tissue remodeling member; and manipulating the exposed tissue remodeling member to remove portions of an internal tissue of the patient to remodel the internal tissue.

17. The method of claim 16, comprising:

removing the tissue remodeling member from the lumen via retraction through the lumen; and placing a guide pin into the patient after the removal of the tissue remodeling member from the lumen.

18. The method of claim 16, wherein the manipulating the exposed tissue remodeling member to remove portions of the internal tissue comprises debriding of bone or other hard tissue of the patient.

19. The method of claim 16, wherein:

the tissue remodeling member comprises a drill bit portion; and comprising rotating the drill bit portion by rotating a stylet attached to the drill bit portion to drill a hole in the internal tissue.

20. The method of claim 16, comprising monitoring, using ultrasound imaging, the penetrating through skin and underlying tissue of the patient with the distal tip of the penetrating needle with the tissue remodeling member sheathed within the lumen.

* * * * *